US008541016B2

(12) United States Patent
Kurisawa et al.

(10) Patent No.: US 8,541,016 B2
(45) Date of Patent: Sep. 24, 2013

(54) CELL-ADHESIVE, ENZYMATICALLY CROSSLINKED FLAVONOID HYDROGELS AND METHODS FOR MAKING SAME

(75) Inventors: Motoichi Kurisawa, Singapore (SG); Fan Lee, Singapore (SG); Joo Eun Chung, Singapore (SG); Pui Yik Chan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/375,097

(22) PCT Filed: May 17, 2010

(86) PCT No.: PCT/SG2010/000185
§ 371 (c)(1),
(2), (4) Date: Nov. 29, 2011

(87) PCT Pub. No.: WO2010/138082
PCT Pub. Date: Dec. 2, 2010

(65) Prior Publication Data
US 2012/0070433 A1    Mar. 22, 2012

Related U.S. Application Data

(60) Provisional application No. 61/213,331, filed on May 29, 2009.

(51) Int. Cl.
*A61F 2/02* (2006.01)
(52) U.S. Cl.
USPC ............................................. 424/425
(58) Field of Classification Search
None
See application file for complete search history.

(56) References Cited

U.S. PATENT DOCUMENTS

| | | | |
|---|---|---|---|
| 6,630,457 | B1 | 10/2003 | Aeschlimann et al. |
| 7,858,080 | B2 | 12/2010 | Chung et al. |
| 8,138,163 | B2 | 3/2012 | Chung et al. |
| 2008/0102052 | A1 | 5/2008 | Chung et al. |
| 2009/0169532 | A1 | 7/2009 | Ying et al. |
| 2010/0074956 | A1 | 3/2010 | Kurisawa et al. |
| 2011/0044992 | A1 | 2/2011 | Ying et al. |
| 2012/0016015 | A1 | 1/2012 | Chung et al. |

FOREIGN PATENT DOCUMENTS

| | | |
|---|---|---|
| EP | 2045248 A1 | 4/2009 |
| WO | WO 2004/063388 A2 | 7/2004 |
| WO | WO 2006/124000 A1 | 11/2006 |
| WO | WO 2007/097710 A1 | 8/2007 |
| WO | WO 2008/153277 A1 | 12/2008 |
| WO | WO 2009/054813 A1 | 4/2009 |
| WO | WO-2009/148405 A1 | 12/2009 |
| WO | WO-2010/138082 A1 | 12/2010 |

OTHER PUBLICATIONS

International Preliminary Report on Patentability dated Jun. 30, 2011 in connection with PCT/SG2010/000185.
International Search Report and Written Opinion mailed Jul. 7, 2010 in connection with PCT/SG2010/000185.
Chapter II Demand and Response to Written Opinion mailed Jul. 7, 2010, filed Mar. 25, 2011, in corresponding PCT Application No. PCT/SG2010/000185.
Second Written Opinion mailed Apr. 8, 2011 in corresponding PCT Application No. PCT/SG2010/000185.
Response to Second Written Opinion mailed Apr. 8, 2011, filed Jun. 8, 2011, in corresponding PCT Application No. PCT/SG2010/000185.
Alsberg et al., Engineering growing tissue. PNAS. Sep. 17, 2002;99(19):12025-30.
Ariga et al., Radical Scavenging Action and Its Mode in Procyanidins B-1 and B-3 from Azuki Beans to Peroxyl Radicals. Agricultural and Biological Chemistry. Oct. 23, 1990;54(10):2499-504.
Bordoni et al., Green tea protection of hypoxia/reoxygenation injury in cultured cardiac cells. The Journal of Nutritional Biochemistry. Feb. 2002;13(2):103-11.
Chai et al., Biomaterials Approach to Expand and Direct Differentiation of Stem Cells. Molecular Therapy. Mar. 2007;15(3): 467-80. Epub Jan. 23, 2007.
Chua et al., Surface functionalization of titanium with hyaluronic acid/chitosan polyelectrolyte multilayers and RGD for promoting osteoblast functions and inhibiting bacterial adhesion. Biomaterials. Apr. 2008;29(10):1412-21. Epub Jan. 10, 2008.
Chung et al., Amplification of Antioxidant Activity of Catechin by Polycondensation with Acetaldehyde. Biomacromolecules. Jan. 2004;5(1):113-8. Epub Nov. 1, 2003.
Drury et al., Hydrogels for tissue engineering: scaffold design variables and applications. Biomaterials. Nov. 2003;24(24):4337-51.
Engler et al., Surface probe measurements of the elasticity of sectioned tissue, thin gels and polyelectrolyte multilayer films: Correlations between substrate stiffness and cell adhesion. Surface Science. Oct. 10, 2004;570(1-2):142-54. Epub Jul. 10, 2004.
Fujimura et al., A lipid raft-associated 67kDa laminin receptor mediates suppressive effect of epigallocatechin-3-O-gallate on Fc?R1 expression. Biochemical and Biophysical Research Communications. Oct. 21, 2005;336(2):674-81. Epub Aug. 29, 2005.
Garbisa et al., Tumor gelatinases and invasion inhibited by the green tea flavanol epigallocatecin-3-gallate. Cancer. Feb. 15, 2001;91(4):822-32.
Garbisa et al., Tumor invasion: molecular shears blunted by green tea. Nature Medicine. Nov. 1999;5(11):1216.
Gerecht et al., Hyaluronic acid hydrogel for controlled self-renewal and differentiation of human embryonic stem cells. PNAS. Jul. 3, 2007;104(27):11298-303.
Hagerman et al., High Molecular Weight Plant Polyphenolics (Tannins) as Biological Antioxidants. Journal of Agricultural and Food Chemistry. May 1998;46(5):1887-92. Epub Apr. 15, 1998.

(Continued)

Primary Examiner — Carlos Azpuru
(74) Attorney, Agent, or Firm — Wolf, Greenfield & Sacks, P.C.

(57) ABSTRACT

There are provided methods for producing a hydrogel that is capable of adhesion of cells and which comprises enzymatically cross-linked conjugates of a hydrogel forming agent and a flavonoid, formed from a reaction using peroxide and peroxidase. Hydrogels produced by such methods and methods of using the hydrogels are also provided.

7 Claims, 17 Drawing Sheets

(56) References Cited

OTHER PUBLICATIONS

Hou et al., Mechanism of action of (−)-epigallocatechin-3-gallate: auto-oxidation-dependent inactivation of epidermal growth factor receptor and direct effects on growth inhibition in human esophageal cancer KYSE 150 cells. Cancer Research. Sep. 1, 2005;65(17):8049-56. Epub Sep. 1, 2005.

Ikeda et al., Tea Catechins with a Galloyl Moiety Suppress Postprandial Hypertriacylglycerolemia by Delaying Lymphatic Transport of Dietary Fat in Rats. The Journal of Nutrition. Feb. 1, 2005;135(2):155-9.

Isemura et al., Tea catechins and related polyphenols as anti-cancer agents. BioFactors. 2000;13(1-4):81-5. Epub Dec. 16, 2008. (The year of publication is sufficiently earlier than the effective U.S. filing date and any foreign priority date so that the particular month of publication is not in issue. See MPEP 609.04(a)).

Jankun et al., Why drinking green tea could prevent cancer. Nature. Jun. 5, 1997;387(6633):561.

Jia et al., Prolongation of sciatic nerve blockade by in situ cross-linked hyaluronic acid. Biomaterials. Aug. 2004;25(19):4797-804.

Jobstl et al., Molecular model for astringency produced by polyphenol protein interactions. Biomacromolecules. May 2004;5(3):942-9. Epub Mar. 13, 2004.

Kobayashi et al., Enzymatic polymerization. Chemical Reviews. Dec. 2001;101(12):3793-818. Epub Nov. 7, 2001.

Kurisawa et al., Enzymatic Synthesis and Antioxidant Properties of Poly(rutin). Biomacromolecules, Sep. 2003;4(5):1394-9. Epub Aug. 14, 2003.

Kurisawa et al., Injectable biodegradable hydrogels composed of hyaluronic acid-tyramine conjugates for drug delivery and tissue engineering. Chemical Communications. 2005;(34):4312-4. Advance Epub Jul. 28, 2005.

Lee et al., An injectable enzymatically crosslinked hyaluronic acid-tyramine hydrogel system with independent tuning of mechanical strength and gelation rate. Soft Matter. 2008;4(4):880-7. Advance Epub Feb. 29, 2008.

Lee et al., An Injectable Hyaluronic Acid-Tyramine Hydrogel System for Protein Delivery. Journal of Controlled Release. Mar. 19, 2009;134(3):186-93. Epub Dec. 7, 2008.

Li et al., Evaluation of the Antioxidant and Pro-oxidant Effects of Tea Catechin Oxypolymers. Journal of Agricultural and Food Chemistry. Dec. 2000;48(2):6362-6. Epub Nov. 28, 2000.

Lill et al., Complex effects of different green tea catechins on human platelets. FEBS Letters. Jul. 10, 2003;546(2-3):265-70. Epub Jun. 2, 2003.

Liu et al., Delivery of interleukin-12 in gelatin hydrogels effectively suppresses development of transplanted colonal carcinoma in mice. Cancer Chemotherapy and Pharmacology. Jan. 2003;51(1):53-7. Epub Nov. 20, 2002.

Mochizuki et al., Kinetic analysis and mechanistic aspects of autoxidation of catechins. Biochim Biophys Acta. Jan. 15, 2002;1569:35-44.

Nagle et al., Epigallocatechin-3-gallate (EGCG): chemical and biomedical perspectives. Phytochemistry. Sep. 2006;67(17):1849-55. Epub Jul. 31, 2006.

Nakagawa et al., Tea Catechin Supplementation Increases Actioxidant Capacity and Prevents Phospholipid Hydroperoxidation in Plasma of Humans. Journal of Agricultural and Food Chemistry. Oct. 1999;47(10):3967-73. Epub Sep. 25, 1999.

Noda et al., Induction of apoptosis by epigallocatechin-3-gallate in human lymphoblastoid B cells. Biochemical and Biophysical Research Communications. Nov. 3, 2007;362(4):951-7. Epub Aug. 24, 2007.

Pan et al., Induction of apoptosis by the oolong tea polyphenol theasinensin A through Cytochrome c release and activation of caspase-9 and caspase-3 in human U937 cells. Journal of Agriculture and Food Chemistry. Dec. 2000;48(12):6337-46. Epub Nov. 22, 2000.

Park et al., Photopolymerized hyaluronic acid-based hydrogels and interpenetrating networks. Biomaterials. Mar. 2003;24(6):893-900.

Qui et al., Environment-sensitive hydrogels for drug delivery. Advanced Drug Delivery Reviews. Dec. 31, 2001;53(3):321-39.

Reich, Pharmaceutical formulation and clinical application. Chapter 10 from Handbook of Therapeutic Antibodies, vol. 1. Ed. Dubel. Wiley-VCH. Weinheim. Mar. 2007:239-65.

Roedig-Penman et al., Antioxidant Properties of Catechins and Green Tea Extracts in Model Food Emulstions. Journal of Agricultural and Food Chemistry. Nov. 1997;45(11):4267-70.

Roginsky et al., Oxidation of tea extracts and tea catechins by molecular oxygen. J Agric Food Chem. Jun. 2005;53(11): 4529-35. Epub Apr. 30, 2005.

Sakanaka et al., Inhibitory Effects of Green Tea Polyphenols on the Production of a Virulence Factor of the Periodontal-Disease-Causing Anaerobic Bacterium *Porphyromonas gingivalis*. Journal of Agricultural and Food Chemistry. Mar. 24, 2004;52(6):1688-92. Epub Feb. 25, 2004.

Sang et al., Autooxidative quinine formation in vitro and metabolite formation in vivo from tea polyphenol (−)-epigallocatechin-3-gallate: studied by real-time mass spectrometry combined with tandem mass ion mapping. Free Radical Biology and Medicine. Aug. 1, 2007;43(3):362-71. Epub Apr. 13, 2007.

Sang et al., Stability of tea polyphenol (−)-epigallocatechin-3-gallate and formation of dimers and epimers under common experimental conditions. J Agric Food Chem. Nov. 30, 2005;53(24):9478-84. Epub Nov. 11, 2005.

Schacht, Polymer chemistry and hydrogel systems. Journal of Physics: Conference Series 3, 2004:22-8. (The year of publication is sufficiently earlier than the effective U.S. filing date and any foreign priority date so that the particular month of publication is not in issue. See MPEP 609.04(a)).

Segura et al., Crosslinked hyaluronic acid hydrogels: a strategy to functionalize and pattern. Biomaterials. Feb. 2005;26(4): 359-71.

Shimizu et al., Nanogel DDS enables sustained release of IL-12 for tumor immunotherapy. Biochemical and Biophysical Research Communications. Mar. 7, 2008;367(2):330-5. Epub Dec. 26, 2007.

Smith et al., Synthetic analogs of green tea polyphenols as proteasome inhibitors. Molecular Medicine. Jul. 2002;8(7):382-92.

Tachibana et al., A receptor for green tea polyphenol EGCG. Nature Structural and Molecular Biology. Apr. 2004;11(4):380-1. Epub Mar. 14, 2004.

Terao et al., Protective Effect of Epicatechin, Epicatechin Gallate, and Quercetin on Lipid Peroxidation in Phospholipid Bilayers. Archives of Biochemistry and Biophysics. Jan. 1994;308(1):278-84.

Tzircotis et al., Chemotaxis towards hyaluronan is dependent on CD44 expression and modulated by cell type variation in CD44-hyaluronan binding. Journal of Cell Science. Nov. 1, 2005;118(21):5119-28.

Yamanaka et al., Green tea catechins such as (−)-epicatechin and (−)-epigallocatechin accelerate $Cu^{2+}$-induced low density lipoprotein oxidation in propagation phase. FEBS Letters. Jan. 20, 1997;401(2):230-4.

Yang et al., Tea and cancer. Journal of National Cancer Institute. Jul. 7, 1993;85(13):1038-49.

Yang et al., Tea and tea polyphenols in cancer prevention. Journal of Nutrition. Feb. 1, 2000;130(2):472S-8S. Presented at the symposium entitled "Diet, Natural Products and Cancer Prevention: Progress and Promise" as part of the Exp Biol 99 mtg held Apr. 17-21 in Washington, DC.

Yen et al., Antioxidant and Pro-Oxidant Effects of Various Tea Extracts. Journal of Agricultural and Food Chemistry. Jan. 1997;45(1):30-4. Abstract published in Adv ACS Abstracts Dec. 1, 1996.

Yeo et al., In situ cross-linkable hyaluronic acid hydrogels prevent post-operative abdominal adhesions in a rabbit model. Biomaterials. Sep. 2006;27(27):4698-705.

Yeung et al., Effects of substrate stiffness on cell morphology, cytoskeletal structure, and adhesion. Cell Motility and the Cytoskeleton. Jan. 2005;60(1):24-34.

Yokozawa et al., Antioxidative Activity of Green Tea Treated with Radical Initator 2,2'-Azobis(2-amidinopropane) Dihydrochloride. Journal of Agricultural and Food Chemistry. Oct. 2000;48(10):5068-73. Epub Sep. 19, 2000.

Zhao et al., Anti-tumor-promoting activity of a polyphenolic fraction isolated from grape seeds in the mouse skin two-stage initiation-promotion protocol and identification of procyanidin B5-3'-gallate as the most effective antioxidant constituent. Carcinogenesis. Sep. 1999;20(9):1737-45.

a b

US 8,541,016 B2

CELL-ADHESIVE, ENZYMATICALLY CROSSLINKED FLAVONOID HYDROGELS AND METHODS FOR MAKING SAME

CROSS-REFERENCE TO RELATED APPLICATIONS

This application is a U.S. National Stage application based on International Application No. PCT/SG2010/000185, filed May 17, 2010, which claims benefit of, and priority from, U.S. provisional patent application No. 61/213,331 filed on May 29, 2009, the contents of which are fully incorporated herein by reference in their entirety.

FIELD OF THE INVENTION

The present invention relates generally to hydrogels comprising conjugates of a hydrogel forming agent and a flavonoid and methods for preparing and using the hydrogels.

BACKGROUND OF THE INVENTION

Flavonoids are one of the most numerous and best-studied groups of plant polyphenols. The flavonoids consist of a large group of low-molecular weight polyphenolic substances naturally occurring in fruits and vegetables, and are an integral part of the human diet. Dried green tea leaves can contain as much as 30% flavonoids by weight, including a high percentage of flavonoids known as catechins (flavan-3-ol derivatives or catechin-based flavonoids), including (−)-epicatechin, (−)-epigallocatechin, (+)-catechin, (−)-epicatechin gallate and (−)-epigallocatechin gallate.

In recent years, these green tea catechins have attracted much attention because they have been recognized to have biological and pharmacological properties, including antibacterial, anti-neoplastic, anti-thrombotic, vasodilatory, anti-oxidant, anti-mutagenic, anti-carcinogenic, anti-hypercholesterolemic, anti-viral and anti-inflammatory properties, which have been demonstrated in numerous human, animal and in vitro studies [30-32]. These biological and pharmacological properties are potentially beneficial in preventing diseases and protecting the stability of the genome. Many of the beneficial effects of catechins are thought to be linked to the antioxidant actions of the catechins [33]. Among the catechins, (−)-epigallocatechin gallate (EGCG), which is a major component of green tea, is thought to have the highest activity, possibly due to the trihydroxy B ring and the gallate ester moiety at the C3 position [34-38]. EGCG has been recognized to have biochemical and pharmaceutical effects including anti-oxidant, anti-carcinogenic, and anti-inflammatory properties [5-7]. EGCG is known to inhibit a vast array of biomedically relevant molecular targets and disease-related cellular process [8] consequently leading to the induction of apoptosis, inhibition of tumour cell growth, and inhibition of angiogenesis [9]. These beneficial bioactivities are attributed mostly to the strong binding ability of EGCG to many biological molecules, including peptides and proteins, which affect various enzyme activities and signal transduction pathways [10]. EGCG is also known as a potent inhibitor of matrix metalloproteinase (MMP) gelatinases [11] which play a crucial role in tumour metastasis.

Studies have found that a high EGCG dosage is required to exert these therapeutic effects. However, high micromolar concentrations of EGCG can not practically be achieved from simple dietary intake [8]. In general, the activity half-life of flavonoids is limited to a few hours inside the body; metabolism of these compounds has not yet been established.

Despite the favourable anti-oxidation and anti-cancer properties of the catechins such as EGCG, it is impractical to achieve a therapeutic level of this compound in the body by directly ingesting a large amount of green tea, due to the inherent volume constraint. That is, in order to obtain a therapeutic or pharmacological benefit from flavonoids through diet alone, it would be necessary to ingest an amount of food and beverage that is larger than is practical to consume. Moreover, pro-oxidant activity has been reported for several flavonoids including EGCG, making ingesting crude green tea directly a less effective means of delivering EGCG [39-41]

On the other hand, a relatively high-molecular fraction of extracted plant polyphenols (procyanidins) and synthetically oligomerized (+)-catechin and rutin have been reported to exhibit enhanced physiological properties such as antioxidant and anti-carcinogenic activity compared to low-molecular weight flavonoids, [42-46] without pro-oxidant effects [47, 48]. However, neither naturally occurring nor synthesized high molecular weight flavonoids are expected to be absorbed and transported to other tissues after ingestion, since these compounds are typically large, form strong complexes with proteins and are resistant to degradation [49].

In cases of flavonoids consumed via oral intake of foods and beverages, the flavonoids may play a role as antioxidants to protect the digestive tract from oxidative damage during digestion. However, flavonoids can be expected to remain only in the digestive tract and thus their beneficial physiological activities are not likely to be utilized in other tissues. Moreover, their strong hydrophobicity as well as their tendency to form complexes with proteins makes parenteral delivery of these compounds difficult.

SUMMARY OF INVENTION

There is presently provided methods for producing a hydrogel comprising conjugates of a hydrogel forming agent and a flavonoid. In one embodiment, there is provided a method for producing a hydrogel capable of adhesion of cells and methods for forming such a hydrogel. The hydrogel is formed from conjugates of a hydrogel forming agent, for example a polymer, and a flavonoid, for example a catechin-based flavonoid, for example epigallocatechin gallate, using a sufficient amount of a peroxidase enzyme, including horseradish peroxidase, to induce, in the presence of a peroxide, for example hydrogen peroxide, sufficient enzymatic cross-linking in the hydrogel to produce a hydrogel capable of adhesion of cells.

In another, embodiment, there is provided methods for producing a hydrogel comprising conjugates of a hydrogel forming agent and a flavonoid without the addition of an exogenous peroxide or peroxidase or without the addition of exogenous peroxide.

There are also provided methods for adhering a cell to a hydrogel, including for inhibiting proliferation of a cancer cell and for proliferating a non-cancer cells and methods of delivering a flavonoid to a cell.

Due to the numerous beneficial biological and pharmacological properties of flavonoids, the present hydrogels may provide a number of therapeutic properties useful for treating a variety of diseases, disorders and conditions including bacterial infections, viral infections, vascular disease, high cholesterol and inflammation.

For example, due to the anti-neoplastic, anti-angiogenesis, anti-oxidant, anti-mutagenic, and anti-carcinogenic properties of flavonoids, the hydrogels described herein may be useful for the treatment of cancer. Conveniently, additional anti-cancer agents may be included within the hydrogel to increase the anti-cancer effect of the hydrogels. The hydrogels may be used in vivo to reduce or prevent proliferation of cancer cells while permitting the survival and proliferation of non-cancer cells. By using a biodegradable agent such as a biodegradable polymer as the hydrogel forming agent, the flavonoid and any additional anti-cancer agent included in the hydrogel can be gradually released as the polymer is degraded and absorbed within the body of a subject.

Thus in one aspect, there is provided a method for producing a hydrogel that is capable of adhesion of cells and which comprises enzymatically cross-linked conjugates of a hydrogel forming agent and a flavonoid, the method comprising combining from about 0.1 mg/ml to about 500 mg/ml of conjugates of the hydrogel forming agent and the flavonoid; from about 0.001 mM to about 50 mM peroxide; and from about 0.001 units/ml to about 10 units/ml peroxidase; thereby producing the hydrogel. In a particular embodiment, the method comprises combining from about 1 mg/ml to about 100 mg/ml of conjugates of the hydrogel forming agent and the flavonoid; from about 0.01 mM to about 5 mM peroxide; and from about 0.01 units/ml to about 10 units/ml peroxidase.

In particular embodiments, the peroxidase may be horseradish peroxidase, the peroxide may be hydrogen peroxide, the flavonoid may be a catechin-based flavonoid. In one embodiment, the flavonoid is epigallocatechin gallate.

In particular embodiments, the hydrogel forming agent is a polymer. In one embodiment, the hydrogel forming agent is hyaluronic acid.

In one embodiment, the method for producing a hydrogel that is capable of adhesion of cells and which comprises enzymatically cross-linked conjugates of a hydrogel forming agent and a flavonoid, further comprises combining a bioactive agent with said conjugates, peroxide and peroxidase. In one embodiment, the bioactive agent may be an anti-cancer agent, including, for example, herceptin.

In another aspect, there is provided a hydrogel capable of adhesion of cells and which comprises enzymatically cross-linked conjugates of a hydrogel forming agent and a flavonoid, the hydrogel produced by a method comprising combining: from about 0.1 mg/ml to about 500 mg/ml of conjugates of the hydrogel forming agent and the flavonoid; from about 0.001 mM to about 50 mM peroxide; and from about 0.001 units/ml to about 10 units/ml peroxidase.

In a particular embodiment the hydrogel capable of adhesion of cells and which comprises enzymatically cross-linked conjugates of a hydrogel forming agent and a flavonoid is produced by combining from about 1 mg/ml to about 100 mg/ml of conjugates of the hydrogel forming agent and the flavonoid; from about 0.01 mM to about 5 mM peroxide; and from about 0.01 units/ml to about 10 units/ml peroxidase;

In particular embodiments, the peroxidase may be horseradish peroxidase, the peroxide may be hydrogen peroxide, the flavonoid may be a catechin-based flavonoid. In one embodiment, the flavonoid is epigallocatechin gallate.

In particular embodiments, the hydrogel forming agent is a polymer. In one embodiment, the hydrogel forming agent is hyaluronic acid.

In one embodiment, the hydrogel that is capable of adhesion of cells and which comprises enzymatically cross-linked conjugates of a hydrogel forming agent and a flavonoid, further comprises a bioactive agent. In one embodiment, the bioactive agent may be an anti-cancer agent, including, for example, herceptin.

In yet another aspect, there is provided a method for adhering a cell to a hydrogel, the method comprising contacting the cell with a hydrogel that is capable of adhesion of cells and which comprises enzymatically cross-linked conjugates of a hydrogel forming agent and a flavonoid, as described herein.

In different embodiments, the cell may be a cancer cell, wherein proliferation of the cancer cell is inhibited or a non-cancer cell wherein the non-cancer cell is proliferated. In different embodiments the cell may be in vitro or in vivo.

In particular embodiments, the method for adhering a cell to a hydrogel described herein comprises administering to a subject the hydrogel comprising an effective amount of the conjugates for the treatment of cancer.

In another aspect, there is provided a method for producing a hydrogel comprising conjugates of a hydrogel forming agent and a flavonoid, the method comprising combining the conjugates in a solution in the absence of an exogenously added peroxide and in the absence of a peroxidase. In particular embodiments, the method comprises controlling the gelation rate of the hydrogel by modifying the pH of the solution. In one embodiment, the pH is modified between 3 and 10. In another embodiment, the pH is modified between 6 and 8. In another particular embodiment, the method comprises adding catalase to the solution.

In yet another aspect, there is provided a method for producing a hydrogel comprising conjugates of a hydrogel forming agent and a flavonoid, the method comprising combining the conjugates and a peroxidase in a solution in the absence of an exogenously added peroxide.

In particular embodiments of the method for producing a hydrogel comprising conjugates of a hydrogel forming agent and a flavonoid, the method comprising combining the conjugates in a solution in the absence of an exogenously added peroxide and in the absence of a peroxidase and the method for producing a hydrogel comprising conjugates of a hydrogel forming agent and a flavonoid, the method comprising combining the conjugates and a peroxidase in a solution in the absence of an exogenously added peroxide. In different embodiments, the flavonoid may be a catechin-based flavonoid, including, for example, epigallocatechin gallate and the hydrogel forming agent may be a polymer, including, for example, hyaluronic acid. In particular embodiments, the concentration of the conjugates in the solution may from about 0.1 mg/ml to about 500 mg/ml. In one embodiment, the concentration of the conjugates in the solution is from about 1 mg/ml to about 100 mg/ml. In still other particular embodiments, the methods may further comprise combining a bioactive agent with the conjugates in the solution. The bioactive agent may be an anti-cancer agent, including, for example, herceptin.

In another aspect, there is provided a hydrogel comprising conjugates of a hydrogel forming agent and a flavonoid, the hydrogel produced by the method for producing a hydrogel comprising conjugates of a hydrogel forming agent and a flavonoid, the method comprising combining the conjugates in a solution in the absence of an exogenously added peroxide and in the absence of a peroxidase, described herein, or the method for producing a hydrogel comprising conjugates of a hydrogel forming agent and a flavonoid, the method comprising combining the conjugates and a peroxidase in a solution in the absence of an exogenously added peroxide, described herein.

In another aspect, there is provided a method for delivering a flavonoid to a cell, the method comprising contacting the hydrogel described in the preceding paragraph with the cell.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
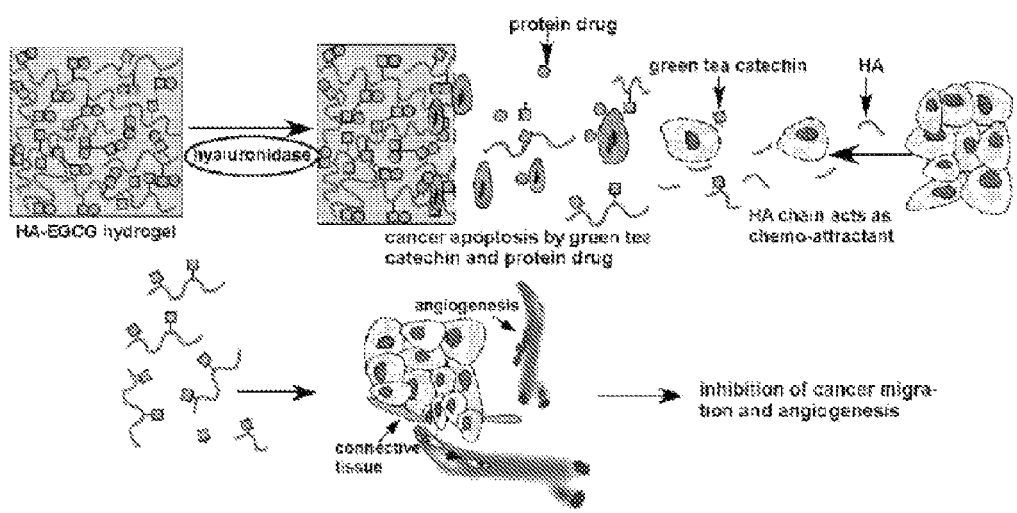
FIG. 1. Schematic illustration of versatile HA-EGCG hydrogel for cancer therapy.

Flavonoids are known to have a variety of beneficial properties, including anti-bacterial, anti-neoplastic, anti-thrombotic, vasodilatory, anti-oxidant, anti-mutagenic, anti-carcinogenic, anti-hypercholesterolemic, anti-viral and anti-inflammatory effects. To increase the availability of beneficial flavonoid compounds, flavonoids may be conjugated to various agents allowing for modification of the physical properties of the flavonoid and augmenting the biological and pharmacological properties of the flavonoid without disrupting the polyphenol structure of the flavonoid.

Conjugation of an agent to a flavonoid can provide a composition that is suitable for administration to a subject by incorporating the flavonoid into a particular vehicle formed with the conjugate, and thus can allow for administration of higher concentrations of flavonoids than can be obtained through diet.

Delivery vehicles comprising such conjugates were previously described in published international application WO 2006/124000 and published US application 2008/102052, the contents of which are herein fully incorporated by reference. Hydrogels comprised of conjugates of a hydrogel forming agent and a flavonoid, referred to herein as flavonoid conjugate hydrogels, are one form of delivery vehicle that can provide improved effective delivery of flavonoids to particular targeted sites in the body.

Hydrogels are highly hydrated suspensions comprised of a cross-linked network of hydrophilic molecules dispersed within water. The structural arrangement of a hydrogel derives from cross-links formed between the molecules by various chemical and physical bonds [51]. Physical crosslinking utilizes physical interactions between polymers to form crosslinks, such as such as ionic, substrate-ligand or hydrophobic interactions. Chemically crosslinked hydrogels, which are usually formed by a Michael-type addition reaction, disulfide bond formation and aldehyde-mediated crosslinking, have improved mechanical properties and stability in comparison to physically crosslinked hydrogels.

Hydrogels have been widely used for drug delivery and as scaffolds in tissue engineering. Particularly, injectable and biodegradable hydrogel systems have received much attention because of the elimination of surgical implantation and retrieval. Hydrogels are a convenient form of delivery vehicle as the cross-linked structure allows for controlled and sustained release of therapeutic agents as well as protection of such agents from degradation by hostile environmental factors such as enzymes and low pH [50]. Recently, gelatin hydrogel and cholesterol-bearing pullulan hydrogel have been developed as carriers for sustained immunoprotein release and suppression of tumor growth in vivo via subcutaneous injection administration [2, 3].

Typically, unmodified hydrogels do not promote cellular adhesion due to their hydrophilic nature [51]. To date, modification of hydrogels with cell binding peptides such as RGD peptides, or proteins such as collagen or gelatin, has been necessary in order to achieve cell adhesion [19, 20].

The present inventors have made the surprising discovery that cells adhere to hydrogels comprised of conjugates of flavonoids and hydrogel forming agents, referred to herein as flavonoid conjugates, and formed by enzymatic cross-linking of the flavonoid conjugates, without the need for modification of the hydrogel with additional components such as cell binding peptides or proteins.

"Enzymatic cross-linking", also referred to herein as "enzyme-catalyzed cross-linking" or "peroxidase-catalyzed cross-linking", refers to the formation of cross-links between flavonoid moieties, particularly oxygen-oxygen cross-links, as the result of an oxidation reaction catalysed by a peroxidase enzyme. This is in contrast to "oxygenic cross-linking", which refers to the formation of cross-linking by oxygenic-oxidation, without any enzyme catalysis, described below.

The term "enzymatically cross-linked" is used herein to describe cross-linking between two or more flavonoid moieties or flavonoid conjugates formed by enzymatic cross-linking, that is cross-linking formed as a result of an oxidation reaction catalysed by a peroxidase enzyme.

Without being limited to any particular theory, it appears that a particular flavonoid moiety may be cross-linked to more than one other flavonoid moiety via enzymatic cross-linking, which may result in the formation of flavonoid oligomers within the formed hydrogel. As used herein, reference to flavonoid oligomers that are the result of the enzymatic cross-linking refers to two or more flavonoid moieties connected via oxygen-oxygen linkages catalysed by a peroxidase enzyme in the presence of peroxide. In the absence of enzymatic cross-linking, flavonoid conjugates undergo oxygenic-oxidation (also known as auto-oxidation) to produce superoxide radicals and flavonoid radicals with unpaired electrons delocalized around the B ring. A chain reaction is propagated by the reaction of the superoxide radicals with the flavonoid radicals resulting in oxygenic cross-linking of the flavonoids to form flavonoid dimers and $H_2O_2$ [9, 21].

In contrast, in the presence of a peroxidase enzyme, such as horseradish peroxidase, and peroxide, the flavonoid moieties within the flavonoid conjugates are cross-linked by enzymatic oxidation (i.e. enzymatic cross-linking). Without being limited to any particular theory, the enzymatic cross-linking process may involve two successive steps: first, the peroxidase is oxidized by peroxide, to form an intermediate; and second, this intermediate then oxidizes a phenolic hydroxyl group on the flavonoid, resulting in the formation of flavonoid oligomers via oxygen-oxygen cross-linking of the phenol groups and the formation of a flavonoid conjugate hydrogel.

As oxygenic cross-linking and enzymatic cross-linking may occur simultaneously, a flavonoid conjugate hydrogel synthesized using a cross-linking peroxidase enzyme may consist of a complex mixture of flavonoid dimers and oligomers. However, enzymatic oxidation occurs more quickly than oxygenic oxidation. Thus, with increasing amounts of perioxidase enzyme, an increasing amount of cross-links between the flavonoid moieties within the hydrogel should be formed by enzymatic cross-linking rather than by oxygenic cross-linking. With a sufficient amount of peroxidase, the available flavonoids may be exhausted by the enzymatic cross-linking thus inhibiting the formation of dimers by oxygenic oxidation of the flavonoids.

The inventors have found that the concentration of peroxidase enzyme, such as horseradish peroxidase, and thus the proportion of enzymatic cross-linking, used in synthesizing the hydrogel affects cell adhesion to the flavonoid conjugate hydrogel. Cell adhesion to a hydrogel formed with sufficient amount of enzymatic cross-linked flavonoid conjugates is possible. In contrast, cells do not adhere to a flavonoid conjugate hydrogel formed only with oxygenic cross-linked flavonoid conjugates.

The ability of a flavonoid conjugate hydrogel to adhere cells thus can be expected to depend on the extent of the enzymatic cross-linking between flavonoid moieties, and accordingly, the amount of peroxidase enzyme, for example horseradish peroxidase (HRP), used in the formation of the flavonoid conjugate hydrogel.

Cell adhesion to the flavonoid conjugate hydrogel described herein may provide improved delivery of flavonoids to a cell. When adhered to the hydrogel, a cell is retained in close proximity to the flavonoid conjugates and any other therapeutic agents contained in and released from the hydrogel. Such "cell trapping" may improve the efficiency and success of flavonoids and additional therapeutic agents reaching the cell.

Thus, there is presently provided, a method for adhering a cell to a hydrogel by contacting the cell to a hydrogel comprising enzymatically cross-linked conjugates of a hydrogel forming agent and a flavonoid. A method for producing such a hydrogel contemplates the use of conjugates of a hydrogel forming agent and a flavonoid, peroxide and peroxidase, all at concentrations sufficient to enzymatically cross-link the flavonoids and produce a hydrogel capable of adhesion of cells. The method may comprise combining from about 0.1 mg/ml to about 500 mg/ml of conjugates of a hydrogel forming agent and a flavonoid; from about 0.001 mM to about 50 mM peroxide; and from about 0.001 units/ml to about 10 units/ml peroxidase; thereby producing a hydrogel that is capable of adhesion of cells and which comprises enzymatically cross-linked conjugates of a hydrogel forming agent and a flavonoid. In another embodiment, the method may comprise combining from about 1 mg/ml to about 100 mg/ml of conjugates of a hydrogel forming agent and a flavonoid; from about 0.01 mM to about 5 mM peroxide; and from about 0.01 units/ml to about 10 units/ml peroxidase; thereby producing a hydrogel that is capable of adhesion of cells and which comprises enzymatically cross-linked conjugates of a hydrogel forming agent and a flavonoid.

As used herein a "hydrogel that is capable of adhesion of cells", is a hydrogel which can adhere cells and from which adherent cells are not readily dislodged upon rinsing with phosphate-buffered saline (PBS).

It will be understood that a small number of cells may adhere to hydrogels not capable of adhesion of cells, for example, the hydrogels in the present Examples formed by only oxygenic cross-linking. However, following rising with PBS, only a minimal number of cells remain adhered to such hydrogels as compared to hydrogels that are capable of adhesion of cells.

Thus, a skilled person can readily determine if a hydrogel is a hydrogel that is capable of adhesion of cells by contacting the hydrogel with cells and subsequently rinsing the cells with PBS and observing the number of remaining adherent cells.

For example, to determine if a hydrogel is capable of cell adhesion, cells may be seeded in 96-well plates coated with the hydrogel to be tested. The cells may then be gently rinsed with approximately 100 µl of the PBS at approximately 37° C. and the number of cells that remain adhered to the hydrogel observed. A hydrogel capable of adhesion of cells, as described herein, is a hydrogel to which a substantial number of the cells remain adhered after rinsing with PBS.

The cells that the presently described hydrogel is capable of adhering or cell that is to be adhered to the presently described hydrogel may be any cell to which a flavonoid or biological agent, including an anti-cancer agent, is desired to be delivered or which is desired to be proliferated or adhered to the described hydrogel. In different embodiments, the cell may be a non-cancer cell, a cancer cell, or a stem cell, as defined below. The cell may be in vitro or in vivo. In one embodiment, the cell may be a cell located in a subject in need of treatment for cancer. In one embodiment, the subject is human.

It will be understood that the extent of enzymatic cross-linking in the hydrogel contemplated herein, and consequently the number of cells adhering to the hydrogel may be varied depending on the intended use of the hydrogel. For example, if the hydrogel is to be used to proliferate non-cancer cells, the hydrogel should contain sufficient enzymatic cross-linking for adhesion of an appropriate number of non-cancer cells to result in the desired cell proliferation on the hydrogel. In another example, if the hydrogel is to be used in the treatment of cancer, the hydrogel should contain sufficient cross-linking for adhesion of an appropriate amount of cancer cells to effectively deliver the therapeutic agents contained in the hydrogel to a sufficient number of cancer cells to achieve the desired result, for example inhibition, slowing or reduction of tumour growth. Furthermore, it will be understood that the extent of enzymatic cross-linking required to achieve adhesion of the desired number of cells may differ depending on the type of cells that are the cells.

Thus, in the hydrogels described herein, the extent of enzymatic cross-linking may be correlated to the number of adherent cells required for the intended use of the hydrogel or the type of cell that is desired to be adhered.

In one embodiment, the extent of enzymatic cross-linking is correlated to the number of cells that can be effectively targeted by the amount of therapeutic agents present in the hydrogel.

In another embodiment, there is provided a method for producing a flavonoid conjugate hydrogel without the addition of an exogenous peroxide or a peroxidase or without the addition of an exogenous peroxide. The presently described method for producing a flavonoid conjugate hydrogel without the addition of a peroxidase may advantageously avoid any possible immunogenicity concerns associated with the use of peroxidase in forming hydrogels.

Formation of Flavonoid Conjugates

As discussed, conjugation of an agent, including a hydrogel forming agent, to a flavonoid can increase the availability of flavonoid compounds while augmenting the flavonoid's biological or pharmacological properties.

The flavonoid conjugate presently described may be comprised of any suitable hydrogel forming agent and any flavonoid, as described below.

A hydrogel forming agent for use in the methods and hydrogels described herein may be any chemical group or moiety that can be conjugated to a flavonoid to form a molecule that is capable of being formed into a hydrogel. Thus, the hydrogel forming agent should be hydrophilic, water insoluble and have good swellability characteristics. Furthermore, it will be understood that the hydrogel forming agent should be non-toxic, biocompatible and suitable for pharmacological use.

The hydrogel forming agent may also have other desirable properties, for example, the hydrogel forming agent may have low immunogenicity, and it may be biodegradable or non-biodegradable depending on the desired biological application of the composition, for example, for controlled release of flavonoids at a particular site in a body.

In different embodiments, the hydrogel forming agent is a protein, polysaccharide, monomer, polymer or copolymer or derivatives, polymers or copolymers thereof.

In one embodiment, the hydrogel forming agent may be a protein including, for example, gelatin.

In another embodiment, the hydrogel forming agent may be a polysaccharide including, for example, dextran or chitosan.

In one embodiment, the hydrogel forming agent may be a hydrophilic monomer including, for example, (2-hydroxyethyl) methacrylate and ethyleneglycol bismethacrylate.

In another embodiment, the hydrogel forming agent may be a copolymer including, for example, poly(lactic-co-glycolic acid)

In particular embodiments the hydrogel forming agent is a polymer including, for example, agarose, poly (ethylene glycol), alginate or hyaluronic acid. In particular embodiments the polymer may be a biodegradable polymer. The polymer may be a natural or a synthetic polymer. The polymer may be chosen to have desired swellability characteristics and to have appropriate groups available for cross-linking of the polymer moieties.

In different embodiments, the polymer may be derived from a single type or species of monomer or may be a copolymer derived from two or more types or species of monomers. In one example, the polymer may be comprised of repeating units of one type of monomer. In another example the polymer may be comprised of alternating units of two or more types of monomers. In still another example, the polymer may be comprised of a sequence of monomers comprised of two or more types of monomers that is repeated throughout the polymer.

In other embodiments, the polymer that is the hydrogel forming agent may be derived from polymers that are combined to form a larger polymer that is the hydrogel forming agent. In different embodiments, the polymers combined to form the polymer that is the hydrogel forming agent are of a single type or species of polymer or of two or more different types of species of polymer. In one embodiment, the polymer that is the hydrogel forming agent is comprised of repeating units of one type of polymer. In another example, one type of polymer may be combined with another type of polymer to form the polymer that is the hydrogel forming agent. In yet another example, a polymer may be combined with a monomer to form the polymer that is the hydrogel forming agent.

In a particular embodiment, the hydrogel forming agent is the polymer hyaluronic acid (HA). In different embodiments, the polymer is aldehyde-derivatized hyaluronic acid, hyaluronic acid conjugated with aminoacetylaldehyde diethylacetal, or either of the aforementioned hyaluronic acid polymers derivatized with tyramine. Methods of synthesizing such HA polymers are known in the art and have been described for example in international application WO 2006/124000 and US application 2008/102052, the content of which are fully incorporated herein.

The flavonoid may be any flavonoid from the general class of molecules derived from a core phenylbenzyl pyrone structure, and includes flavones, isoflavones, flavanols, flavanones, flavan-3-ols, catechins, anthocyanidins and chalcones.

In particular embodiments the flavonoid is a catechin or a catechin-based flavonoid. A catechin, or a catechin-based flavonoid is any flavonoid that belongs to the class generally known as catechins (or flavan-3-ol derivatives), and includes catechin and catechin derivatives, including epicatechin, epigallocatechin, catechin, epicatechin gallate and epigallocatechin gallate, and including all possible stereoisomers of catechins or catechin-based flavonoids. In particular embodiments, the catechin-based flavonoid is (+)-catechin or (−)-epigallocatechin gallate. In a particular embodiment, the catechin-based flavonoid is epigallocatechin gallate.

A catechin-based flavonoid to be conjugated to a hydrogel forming agent may be a single monomeric unit of a catechin-based flavonoid or it may be an oligomer of one or more catechin-based flavonoids. As stated above, conjugation of a hydrogel forming agent to a flavonoid can result in augmentation of the flavonoid's biological or pharmacological properties. Furthermore, oligomers of catechin-based flavonoids tend to have amplified or augmented levels of the biological and pharmacological properties associated with catechin-based flavonoids, and may even have reduced pro-oxidant effects that are sometimes associated with monomeric catechin-based flavonoids. Thus in one embodiment, an oligomerized catechin-based flavonoid having amplified or augmented flavonoid properties is conjugated to the hydrogel forming agent.

Oligomers of catechin-based flavonoids that can be conjugated to hydrogel forming agents, such as polymers, are known, and include oligomers prepared through enzyme-catalyzed oxidative coupling and through aldehyde-mediated oligomerization, for example as described in published international application WO 2006/124000 and published US application 2008/102052, the contents of which are fully incorporated by reference herein.

An aldehyde-mediated oligomerization process results in an unbranched oligomer that has defined linkages, for example through carbon-carbon linkages such as $CH-CH_3$ bridges linked from the C6 or C8 position on the A ring of one monomer to the C6 or C8 position on the A ring of the next monomer, including in either possible stereoconfiguration, where applicable. Thus, the $CH-CH_3$ linkage may be between the C6 position of the A ring of one monomer and either of the C6 or C8 position of the next monomer or it may be between the C8 position of the A ring of the first monomer and either of the C6 or C8 position of the next monomer.

The oligomer of catechin-based flavonoid to be conjugated to the hydrogel forming agent, for example a polymer, may be of 2 or more monomeric units linked together. In certain embodiments, the catechin-based flavonoid oligomer has from 2 to 100 monomer units, from 10 to 100, from 2 to 80, from 10 to 80, from 2 to 50, from 10 to 50, from 2 to 30, from 10 to 30, from 20 to 100, from 30 to 100 or from 50 to 100 monomeric units.

The hydrogel forming agent may be conjugated to the flavonoid by any suitable means known in the art that provides attachment of the hydrogel forming agent to the flavonoid to form a conjugate capable of being formed into a hydrogel, while maintaining or augmenting the biological and pharmacological properties of the flavonoid and without disruption of the polyphenol structure of the flavonoid.

In one embodiment, a hydrogel forming agent may be conjugated to a flavonoid by "aldehyde mediated conjugation" wherein the hydrogel forming agent is reacted with the flavonoid in the presence of an acid catalyst, the hydrogel forming agent having a free aldehyde group, or a group that is able to be converted to a free aldehyde group in the presence of acid. Aldehyde-mediated conjugation of a hydrogel forming agent to a flavonoid can result in attachment of the hydrogel forming agent at the C6 and/or C8 position of the flavonoid A ring, which does not disrupt or affect the B and C rings of the flavonoid or the various hydroxyl groups on the flavonoid. Formation of flavonoid conjugates by aldehyde mediated conjugation is described in published international application WO 2006/124000 and published US application 2008/102052, the contents of which are fully incorporated by reference herein.

In a particular embodiment, the flavonoid conjugate is comprised of polymer conjugated to a catechin-based flavonoid and the conjugation is carried out by aldehyde mediated conjugation as defined above. Thus, the conjugation reaction may involve conjugation of a polymer containing a free aldehyde group or a group that is able to be converted to a free aldehyde group in the presence of acid to a catechin-based flavonoid.

The polymer may be any chemical group or moiety having a free aldehyde group prior to conjugation with the catechin-based flavonoid, or having a group that is converted to an aldehyde group in the presence of acid, for example an acetal group, and that can be incorporated into a hydrogel. The polymer may also be any biological polymer, modified to contain a free aldehyde group or a group that is convertible to an aldehyde in the presence of acid, for example an aldehyde-modified protein, peptide, polysaccharide or nucleic acid.

The free aldehyde group on the polymer allows for the conjugation of the polymer in a controlled manner to either the C6 or the C8 position of the A ring, or both, of the flavonoid structure, thus preventing disruption of the flavonoid structure, particularly the B and C rings of the flavonoid, and thus preserving the beneficial biological and pharmacological properties of the flavonoid. The polymer is conjugated to the catechin-based flavonoid via a reaction of the aldehyde group of the polymer with the C6 and/or the C8 position of the A ring of the catechin-based flavonoid.

The flavonoid conjugate may be synthesized using acid catalysis of a condensation of the aldehyde group of the polymer with the catechin-based flavonoid, or using acid to convert a functional group on the polymer to a free aldehyde prior to condensation of the aldehyde group with the catechin-based flavonoid.

To conjugate the polymer and the catechin-based flavonoid, the polymer and the catechin-based flavonoid may be separately dissolved in a suitable solvent. The polymer with the free aldehyde is added, for example by dropwise addition, to the solution containing the catechin-based flavonoid, in the presence of an acid, for example at a pH from about 1 to about 5, or for example at pH of about 1. The reaction is allowed to go to completion. Following the conjugation reaction, excess unreacted catechin-based flavonoid can be removed from the conjugated composition, for example by dialysis or by molecular sieving.

In another embodiment, the polymer may be dissolved in deionized or distilled water and mixed with a solution comprising the catechin-based flavonoid dissolved in dimethyl sulfoxide (DMSO). The pH of the solution is adjusted to about 1 by addition of an acid, for example HCl and the reaction is allowed to go to completion, for example by stirring at room temperature for about 24 hours. Following the conjugation reaction, the conjugate may be purified from the solution, for example by dialysis.

The ratio of flavonoid to hydrogel forming agent, may be varied, so that there is only one hydrogel forming agent moiety attached to the flavonoid, or so that there is a flavonoid attached at more than one position on the hydrogel forming agent or so that the flavonoid has two hydrogel forming agent moieties attached, for example one at either of the C6 and C8 positions of a catechin-based flavonoid.

The ratio of hydrogel forming agent to flavonoid in the conjugate can be controlled through the ratio of starting reagents. For example, when the molar ratio of hydrogel forming agent to flavonoid is about 1, a single hydrogel forming agent moiety will be attached to a single flavonoid moiety (either monomeric or oligomeric may be used). However, at higher concentrations of hydrogel forming agent, for example at a 10:1 molar ratio of hydrogel forming agent to flavonoid, a composition having a tri-block structure of hydrogel forming agent-flavonoid-hydrogel forming agent may be obtained.

Similarly, the degree of conjugation of the hydrogel forming agent with the flavonoid can be varied by varying the concentrations of hydrogel forming agent and flavonoid in the conjugation reaction. The "degree of conjugation" as used herein refers to the number of flavonoid molecules per 100 units of hydrogel forming agent. For example, a 50% degree of conjugation means that there are 50 flavonoid molecules per 100 units of hydrogel forming agent.

In a particular example, since hyaluronic acid (HA) has multiple sites that may react with a flavonoid during the conjugation reaction, by varying the concentration of the flavonoid in the starting reaction, it is possible to vary the degree of conjugation between the HA polymer and the flavonoid.

For certain hydrogel forming agents, including HA, conjugation to a flavonoid may be accomplished by conversion of particular groups on the hydrogel forming agent to groups that are capable of conjugation with a flavonoid. For example, the conjugation of a HA polymer with a catechin-based flavonoid may be accomplished by conversion of groups on the HA polymer to free aldehyde groups.

The ratio of hydrogel forming agent to flavonoid in the starting reagents for forming the flavonoid conjugates may be varied to adjust the degree of conjugation of the hydrogel forming agent with the flavonoid in the resulting flavonoid conjugates and thus the ratio of hydrogel forming agent to flavonoid present in a hydrogel formed from these flavonoid conjugates. Alternatively, additional hydrogel forming agent that has not been conjugated can be added to the solution for forming a hydrogel prior to cross-linking of the hydrogel so that some of the hydrogel forming agent molecules in the hydrogel will not be conjugated to the flavonoid.

In one embodiment, the flavonoid conjugates used in forming the flavonoid hydrogel have a degree of conjugation of from about 1% to about 90%. In another embodiment, the flavonoid conjugates used in forming the flavonoid hydrogel have a degree of conjugation o of from about 1% to about 50%. In another embodiment, the flavonoid conjugates used in forming the flavonoid hydrogel have a degree of conjugation of from about 2% to about 10%.

In a particular embodiment, the flavonoid conjugate is a conjugate of HA and EGCG and the conjugate is synthesized in a two-step procedure. In the first step protected aldehyde groups are introduced to HA by conjugating diethoxyethyl amine (DA) to HA though NHS/EDC chemistry. The resulting conjugates, HA-DA, generally have a substitution degree (number of carboxyl groups converted to DA in every 100 disaccharide unit) of 10%. HA-DA is then deprotected at a pH of 1 to allow conjugation of EGCG to the aldehyde groups. The conjugation degree of EGCG may be between 1 to 2.5% in the dimer conformation. The resulting HA-EGCG conjugate is soluble in water and can form hydrogels via the crosslinking of the EGCG moieties.

Formation of the Flavonoid Conjugate Hydrogel

There is presently provided a method for forming a hydrogel capable of adhesion of cells comprising enzymatically cross-linked flavonoid conjugates (referred to herein as an "enzymatically cross-linked flavonoid conjugate hydrogel"). The flavonoid conjugates may be a conjugate of any suitable hydrogel forming agent and any suitable flavonoid as describe herein. In one embodiment, the flavonoid conjugate is a conjugate of a polymer and a catechin-based flavonoid. In a particular embodiment, the flavonoid conjugate is a conjugate of hyaluronic acid and epigallocatechin gallate.

To form the enzymatically cross-linked flavonoid conjugate hydrogel described herein, the flavonoid conjugates are cross-linked using a sufficient amount of peroxidase enzyme, and peroxide to form a hydrogel with sufficient enzymatic cross-linking for adhesion of cells to the hydrogel.

Thus, the method comprises combining (i) conjugates of a hydrogel forming agent and a flavonoid; (ii) a peroxide; and (iii) a peroxidase all at concentrations that provide sufficient enzymatic cross-linking between the conjugates for adhesion of cells to the hydrogel. It will be readily understood that the ratio of hydrogel forming agent to flavonoid in the hydrogel and the degree of conjugation of the hydrogel forming agent with the flavonoid may affect the concentrations of flavonoid conjugates, peroxide and peroxidase required to form a hydrogel with sufficient enzymatic cross-linking of the flavonoid conjugates for adhesion of cells.

As discussed above, enzymatic cross-linking of the flavonoid conjugates is formed by oxidation catalysed by a peroxidase enzyme. The peroxidase used may be any peroxidase enzyme that can catalyse reduction of peroxide, and thus result in concomitant oxidation and thus cross-linking between two phenolic hydroxyl groups on flavonoid moieties within the conjugates when used in the present methods. In different embodiments, the peroxidase may be horseradish peroxidase, pegylated horse radish peroxidase or laccase. Conveniently, the peroxidase enzyme may be horse radish peroxidase (HRP), which may be readily purchased.

The peroxidase enzyme is mixed with the flavonoid conjugates together with a peroxide in order to effect enzymatic cross-linking of the conjugates to form the enzymatically cross-linked flavonoid conjugate hydrogel as described herein.

The peroxide may be any form of peroxide that can act as a substrate for the peroxidase enzyme to activate the cross-linking activity of the peroxidase enzyme. In particular embodiments, the peroxide used is hydrogen peroxide, $H_2O_2$.

The concentration of peroxidase enzyme used in the synthesis of a flavonoid conjugate hydrogel can affect the amount of enzymatic cross-linking present in the hydrogel. Thus, the peroxidase enzyme is provided at a concentration that will result in sufficient amount of enzymatic cross-linking in the flavonoid conjugate hydrogel to achieve adhesion of cells.

It will be understood by a person skilled in the art that the concentration of peroxidase enzyme required to form a sufficient amount of enzymatic cross-linking in a flavonoid conjugate hydrogel for adhesion of cells will vary depending on a number of factors including the type and concentration of the hydrogel forming agent, the type and concentration of the flavonoid, the type and concentration of flavonoid conjugates, the ratio of hydrogel forming agent to flavonoid in the hydrogel, the degree of conjugation of the hydrogel forming agent with the flavonoid, the concentration of peroxide, the temperature at which the hydrogel is synthesized or the pH at which the hydrogel is synthesized.

For example, the above factors may affect the rate of enzymatic cross-linking and thus the amount of peroxidase enzyme required to form a sufficient amount of enzymatic cross-linking in the flavonoid conjugate hydrogel for adhesion of cells.

The present inventors have discovered that a flavonoid conjugate hydrogel comprising a sufficient amount of enzymatic cross-linking for adhesion of cells may be formed by mixing: from about 0.1 mg/ml to about 500 mg/ml of conjugates of a hydrogel forming agent and a flavonoid, from about 0.001 mM to about 50 mM peroxide; and from about 0.001 units/ml to about 10 units/ml peroxidase.

Thus there is presently provided, a method for producing a hydrogel that is capable of adhesion of cells and which comprises enzymatically cross-linked conjugates of a hydrogel forming agent and a flavonoid, the method comprising combining from about 0.1 mg/ml to about 500 mg/ml of conjugates of the hydrogel forming agent and the flavonoid from about 0.001 mM to about 50 mM peroxide; and from about 0.001 units/ml to about 10 units/ml peroxidase; thereby producing the hydrogel.

In different embodiments, the concentration of flavonoid conjugates may be from about 0.1 mg/ml to about 500 mg/ml, from about 1 mg/ml to about 100 mg/ml, at least about 0.1 mg/ml, at least about 0.3 mg/ml, at least about 0.5 mg/ml, at least about 0.7 mg/ml, at least about 1 mg/ml, at least about 5 mg/ml, at least about 10 mg/ml, at least about 15 mg/ml, at least about 17 mg/ml, at least about 17.5 mg/ml, at least about 20 mg/ml, at least about 25 mg/ml, at least about 30 mg/ml, at least about 35 mg/ml, at least about 40 mg/ml, at least about 45 mg/ml, at least about 50 mg/ml, at least about 55 mg/ml, at least about 60 mg/ml, at least about 65 mg/ml, at least about 70 mg/ml, at least about 75 mg/ml, at least about 80 mg/ml, at least about 85 mg/ml, at least about 90 mg/ml, at least about 95 mg/ml, at least about 100 mg/ml, at least about 200 mg/ml, at least about 250, at least about 300 mg/ml, at least about 350 mg/ml, at least about 400 mg/ml, at least about 450 mg/ml, at least about 500 mg/ml; the concentration of peroxide may be from about 0.001 mM to about 50 mM, from about 0.01 mM to about 5 mM, at least about 0.001 mM, at least about 0.003 mM, at least about 0.005 mM, at least about 0.007 mM, at least about 0.01 mM, at least about 0.014 mM, at least about 0.02 mM, at least about 0.03 mM, at least about 0.04 mM, at least about 0.05 mM, at least about 0.06 mM, at least about 0.07 mM, at least about 0.08 mM, at least about 0.09 mM, at least about 0.1 mM, at least about 0.2 mM, at least about 0.3 mM, at least about 0.4 mM, at least about 0.5 mM, at least about 0.6 mM, at least about 0.7 mM, at least about 0.8 mM, at least about 0.9 mM, at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 10 mM, at least about 15 mM, at least about 20 mM, at least about 25 mM, at least about, 30 mM, at least about 35 mM, at least about 40 mM, at least about 45 mM, at least about 50 mM; and the concentration of peroxidase may be from about 0.001 units/ml to about 10 units/ml, from about 0.01 units/ml to about 10 units/ml, at least about 0.001 units/ml, at least about 0.003 units/ml, at least about 0.005 units/ml, at least about 0.007 units/ml, at least about 0.01 units/ml, at least about 0.02 units/ml, at least about 0.03 units/ml, at least about 0.04 units/ml, at least about 0.05 units/ml, at least about 0.06 units/ml, at least about 0.07 units/ml at least about 0.08 units/ml, at least about 0.09 units/ml, at least about 0.1 units/ml, at least about 0.5 units/ml, at least about 1.0 units/ml, at least about 1.5 units/ml, at least about 2 units/ml, at least about 2.3 units/ml, at least about 2.5 units/ml, at least about 3.0 units/ml, at least about 3.2 units/ml, at least about 3.5 units/ml, at least about 4.0 units/ml, at least about 4.1 units/ml, at least about 4.5 units/ml, at least about 4.9 units/ml, at least about 5.0 units/ml, at least about 5.5 units/ml, at least about 6.0 units/ml, at least about 6.5 units/ml, at least about 7.0 units/ml, at least about 7.5 units/ml, at least about 8.0 units/ml, at least about 8.5 units/ml, at least about 9.0 units/ml, at least about 9.5 units/ml, or at least about 10 units/ml. In alternative embodiments, there is provided any combination of the concentrations of flavonoid conjugates, concentrations of peroxide and concentrations of peroxidase provided herein.

Alternatively, the concentration of flavonoid conjugates may be from about 0.1 mg/ml to about 500 mg/ml, from about 1 mg/ml to about 100 mg/ml, at least about 0.1 mg/ml, at least about 0.3 mg/ml, at least about 0.5 mg/ml, at least about 0.7 mg/ml, at least about 1 mg/ml, at least about 5 mg/ml, at least about 10 mg/ml, at least about 15 mg/ml, at least about 17 mg/ml, at least about 17.5 mg/ml, at least about 20 mg/ml, at least about 25 mg/ml, at least about 30 mg/ml, at least about 35 mg/ml, at least about 40 mg/ml, at least about 45 mg/ml, at least about 50 mg/ml, at least about 55 mg/ml, at least about 60 mg/ml, at least about 65 mg/ml, at least about 70 mg/ml, at least about 75 mg/ml, at least about 80 mg/ml, at least about 85 mg/ml, at least about 90 mg/ml, at least about 95 mg/ml, at least about 100 mg/ml, at least about 200 mg/ml, at least about 250, at least about 300 mg/ml, at least about 350 mg/ml, at least about 400 mg/ml, at least about 450 mg/ml, at least about 500 mg/ml. Alternatively, the concentration of peroxide may be from about 0.001 mM to about 50 mM, from about 0.01 mM to about 5 mM, at least about 0.001 mM, at least about 0.003 mM, at least about 0.005 mM, at least about 0.007 mM, at least about 0.01 mM, at least about 0.014 mM, at least about 0.02 mM, at least about 0.03 mM, at least about 0.04 mM, at least about 0.05 mM, at least about 0.06 mM, at least about 0.07 mM, at least about 0.08 mM, at least about 0.09 mM, at least about 0.1 mM, at least about 0.2 mM, at least about 0.3 mM, at least about 0.4 mM, at least about 0.5 mM, at least about 0.6 mM, at least about 0.7 mM, at least about 0.8 mM, at least about 0.9 mM, at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 10 mM, at least about 15 mM, at least about 20 mM, at least about 25 mM, at least about, 30 mM, at least about 35 mM, at least about 40 mM, at least about 45 mM, at least about 50 mM. Alternatively, the concentration of peroxidase may be from about 0.001 units/ml to about 10 units/ml, from about 0.01 units/ml to about 10 units/ml, at least about 0.001 units/ml, at least about 0.003 units/ml, at least about 0.005 units/ml, at least about 0.007 units/ml, at least about 0.01 units/ml, at least about 0.02 units/ml, at least about 0.03 units/ml, at least about 0.04 units/ml, at least about 0.05 units/ml, at least about 0.06 units/ml, at least about 0.07 units/ml at least about 0.08 units/ml, at least about 0.09 units/ml, at least about 0.1 units/ml, at least about 0.5 units/ml, at least about 1.0 units/ml, at least about 1.5 units/ml, at least about 2 units/ml, at least about 2.3 units/ml, at least about 2.5 units/ml, at least about 3.0 units/ml, at least about 3.2 units/ml, at least about 3.5 units/ml, at least about 4.0 units/ml, at least about 4.1 units/ml, at least about 4.5 units/ml, at least about 4.9 units/ml, at least about 5.0 units/ml, at least about 5.5 units/ml, at least about 6.0 units/ml, at least about 6.5 units/ml, at least about 7.0 units/ml, at least about 7.5 units/ml, at least about 8.0 units/ml, at least about 8.5 units/ml, at least about 9.0 units/ml, at least about 9.5 units/ml, or at least about 10 units/ml.

In one embodiment, the concentration of the flavonoid conjugates is from about 1 mg/ml to about 100 mg/ml, the concentration of the peroxide is from about 0.01 mM to about 5 mM and the concentration of the peroxidase is from about 0.01 units/ml to about 10 units/ml.

There is also presently provided a hydrogel capable of adhesion of cells and which comprises enzymatically cross-linked conjugates of a hydrogel forming agent and a flavonoid, the hydrogel produced by a method comprising combining from about 0.1 mg/ml to about 500 mg/ml of conjugates of the hydrogel forming agent and the flavonoid;

from about 0.001 mM to about 50 mM peroxide; and from about 0.001 units/ml to about 10 units/ml peroxidase.

In one embodiment, the hydrogel is formed by combining from about 1 mg/ml to about 100 mg/ml of conjugates of a hydrogel forming agent and a flavonoid; from about 0.01 mM to about 5 mM peroxide; and from about 0.01 units/ml to about 10 units/ml peroxidase.

It will be understood that the amount of enzymatic cross-linking that will be sufficient for adhesion of cells may vary depending on the type of cell to be adhered. For example, adhesion of non-cancer cells to the hydrogel may require a different amount of enzymatic cross-linking than adhesion of cancer cells. In addition, the incorporation of bioactive agents may affect the amount of enzymatic cross-linking that will be required for adhesion of cells.

It will be understood that the amount of enzymatic cross-linking may be modified to provide adhesion of an appropriate number of cells to the hydrogel to achieve a desired result. For example, the enzymatically cross-linked flavonoid conjugate hydrogel described herein may be produced such that it comprises a sufficient amount of enzymatic cross-linking to adhere an appropriate number of cells to result in cell proliferation on the hydrogel. In another example, the enzymatically cross-linked flavonoid conjugate hydrogel described herein may be produced such that it comprises a sufficient amount of enzymatic cross-linking to adhere an appropriate amount of cells to the hydrogel that can be treated by the amount of flavonoid and any other active agent present in the hydrogel. In another embodiment, the enzymatically cross-linked flavonoid conjugate hydrogel described herein may be produced such that it comprises a sufficient amount of enzymatic cross-linking to adhere an appropriate amount of cells to the hydrogel for treatment of a disease or disorder by the flavonoids or active agent present in the hydrogel. In a particular embodiment, the enzymatically cross-linked flavonoid conjugate hydrogel described herein may be produced such that it comprises a sufficient amount of enzymatic cross-linking to adhere an appropriate amount of cancer cells to the hydrogel for the treatment of cancer.

A person skilled in the art can use known methods and techniques to determine, based on the above factors, the relative concentration of flavonoid conjugates, peroxidase enzyme, and peroxide required to form a sufficient amount of enzymatic cross-linking for adhesion of cells or for adhesion of an appropriate number of cells for a desired result. For instance, whether a sufficient amount of enzymatic cross-linking is contained within a specific hydrogel preparation for adhesion of cells can readily be determined by culturing cells in the presence of the hydrogel, for example as described in the following Examples, and using techniques known in the art to determine or monitor cell adhesion, proliferation or viability. Furthermore, a skilled person would be able to determine the appropriate conditions, such as concentration of peroxide and concentration of flavonoid conjugates, required to synthesize a hydrogel.

In a particular embodiment, the flavonoid conjugates are hyaluronic acid-epigallocatechin gallate (HA-EGCG) conjugates, the peroxidase is horseradish peroxidase and the peroxide is hydrogen peroxide. HA, a major component of the extracellular matrix, is a desirable backbone polymer for hydrogels due to its high biocompatibility and biodegradability [15]. Furthermore, HA is a chemoattractant and may direct cells, such as cancer cell, to migrate towards the hydrogel [14]. EGCG can bind proteins, and thus an HA-EGCG hydrogel can provide the advantage of protein-EGCG interaction [12] for immobilizing proteins, such as bioactive agents, in the gel, which can be combined with the therapeutic benefits of EGCG.

Thus in one embodiment, a hyaluronic acid-epigallocatechin gallate (HA-EGCG) hydrogel is formed by mixing HA-EGCG conjugates with horseradish peroxidase in the presence of hydrogen peroxide. In a particular embodiment, the concentration of the HA-EGCG conjugates is from about 0.1 mg/ml to about 500 mg/ml, the concentration of hydrogen peroxide is from about 0.001 mM to about 50 mM; and the concentration of horseradish peroxidase is from about 0.001 units/ml to about 10 units/ml peroxidase. In another embodiment, the concentration of the HA-EGCG conjugates is at least about 17.5 mg/ml, the concentration of the hydrogen peroxide is at least about 0.014 mM, and the concentration of the horseradish peroxidase is at least about 2.3 units/ml.

The flavonoid conjugates may be combined with the peroxidase and peroxide using any suitable method known in the art. For example, a solution containing the flavonoid conjugates may be prepared or obtained first. The flavonoid conjugate solution may be prepared in any suitable manner, for example by providing the flavonoid conjugate solution in Dulbecco's Modified Eagle's Medium containing 10% fetal bovine serum. The peroxidase and peroxide may then be added to the flavonoid conjugate solution.

Subsequent to the addition of the peroxidase and peroxide, the solution may be quickly poured into a mold to form a desired shape before the cross-linking reaction is completed. For example, the hydrogel may be formed into a slab suitable for application as a wound dressing. Alternatively, the hydrogel may be formed within the same vessel in which the peroxidase, peroxide and flavonoid conjugate solution are combined. For example, the peroxidase, peroxide and the flavonoid conjugate solution may be combined in a cell culture plate and the hydrogel formed within that culture plate.

The components of the hydrogel may also be injected and reacted to form the hydrogel in vivo, for example in a living tissue, organism or living body including a human living body. Hydrogels may be formed in vivo by injecting the uncross-linked flavonoid conjugates together with the cross-linking enzyme and enzyme activator, or injecting the mixture of the components prior to completion of the cross-linking reaction. Such a hydrogel is useful for drug delivery to a specific site in a body, or for tissue engineering.

In another embodiment, there is provided a method for producing a hydrogel comprising conjugates of a hydrogel forming agent and a flavonoid, the method comprising combining the conjugates in a solution in the absence of an exogenously added peroxide and in the absence of a peroxidase.

The present inventors have discovered that flavonoid conjugate hydrogels can be formed through air auto-oxidation without the addition of peroxide or peroxidase. Forming the hydrogels through air auto-oxidation, without the use of peroxidase, may advantageously avoid possible immunogenicity concerns associated with some peroxidases, such as horseradish peroxidase.

Furthermore, the gelation rate and stiffness of the flavonoid conjugate hydrogels formed by this method [herein referred to as "auto-oxidation flavonoid conjugate hydrogel"] may be controlled by modifying the pH of the solution comprising the flavonoid conjugates. EGCG undergoes oxidation in the presence of di-oxygen molecules to form EGCG quinone and hydrogen peroxide ($H_2O_2$) [52-55] and the EGCG quinone can react with EGCG to form EGCG dimer. The rate of oxidation has been shown to increase with pH [52]. The present inventors have discovered that the gelation rate of the auto-oxidation flavonoid conjugate hydrogel described herein may be reduced by increasing the pH of the solution comprising the flavonoid conjugates. In particular embodiments, the gelation rate of the auto-oxidation flavonoid conjugate hydrogel described herein may be controlled by modifying the pH of the solution comprising the flavonoid conjugates between from about 3 to about 10. In one embodiment, the gelation rate of the auto-oxidation flavonoid conjugate hydrogel described herein may be controlled by modifying the pH of the solution between from about 6 to about 8. A skilled person would be able to adjust the pH of the hydrogel, within the ranges described herein, to achieve a desired gelation rate.

In a particular embodiment, the method for producing the auto-oxidation flavonoid conjugate hydrogel described herein without the addition of an exogenous peroxide or a peroxidase may further comprise addition of catalase to the solution comprising the flavonoid conjugates. Catalase is an enzyme that catalyzes the decomposition of hydrogen peroxide to water and oxygen. In particular embodiments, catalase may be added to the solution comprising the flavonoid conjugates to remove the $H_2O_2$ generated during air-autoxidation of the flavonoid conjugates and reduce the gelation time of the flavonoid conjugate hydrogel.

In another embodiment, there is provided a method for producing a hydrogel comprising conjugates of a hydrogel forming agent and a flavonoid, the method comprising combining the conjugates and a peroxidase in a solution in the absence of an exogenously added peroxide.

Peroxidases, including, for example, horseradish peroxidase, are able to catalyze a variety of substrates, including flavonoids, including EGCG, through reaction with $H_2O_2$. This reaction has been explored to form hydrogels rapidly by using tyramine as the crosslinking moiety [56]. Typically, exogenous $H_2O_2$ needs to added to initiate the enzymatic reaction, as in the case of hyaluronic acid-tyramine hydrogel system. The present inventors have shown that $H_2O_2$ generated as a result of air-autoxidation of flavonoid conjugates can be used for the peroxidase-mediated crosslinking reactions, thus eliminating the need for exogenously added $H_2O_2$.

In different embodiments of the methods of forming an auto-oxidation flavonoid conjugate hydrogel described herein the concentration of flavonoid conjugates in the solution may be from about 0.1 mg/ml to about 500 mg/ml, from about 1 mg/ml to about 100 mg/ml, at least about 0.1 mg/ml, at least about 0.3 mg/ml, at least about 0.5 mg/ml, at least about 0.7 mg/ml, at least about 1 mg/ml, at least about 5 mg/ml, at least about 10 mg/ml, at least about 15 mg/ml, at least about 17 mg/ml, at least about 17.5 mg/ml, at least about 20 mg/ml, at least about 25 mg/ml, at least about 30 mg/ml, at least about 35 mg/ml, at least about 40 mg/ml, at least about 45 mg/ml, at least about 50 mg/ml, at least about 55 mg/ml, at least about 60 mg/ml, at least about 65 mg/ml, at least about 70 mg/ml, at least about 75 mg/ml, at least about 80 mg/ml, at least about 85 mg/ml, at least about 90 mg/ml, at least about 95 mg/ml, at least about 100 mg/ml, at least about 200 mg/ml, at least about 250, at least about 300 mg/ml, at least about 350 mg/ml, at least about 400 mg/ml, at least about 450 mg/ml, at least about 500 mg/ml.

There is also provided a hydrogel comprising conjugates of a hydrogel forming agent and a flavonoid, the hydrogel produced by the method described herein for producing a hydrogel comprising conjugates of a hydrogel forming agent and a flavonoid, the method comprising combining the conjugates in a solution in the absence of an exogenously added peroxide and in the absence of a peroxidase.

Also provided is a hydrogel comprising conjugates of a hydrogel forming agent and a flavonoid, the hydrogel produced by the method described herein for producing a hydrogel comprising conjugates of a hydrogel forming agent and a flavonoid, the method comprising combining the conjugates with a peroxidase in a solution in the absence of an exogenously added peroxide.

Optionally, a bioactive agent may be incorporated in the flavonoid conjugate hydrogels described herein, including by mixing in the solution prior to cross-linking or by addition after formation of the hydrogel.

The bioactive agent may be any agent that has a biological, pharmacological or therapeutic effect in a body, and includes without limitation a protein, a nucleic acid, a small molecule or a drug. A bioactive agent that is a protein may be for example a peptide, an antibody, a hormone, an enzyme, a growth factor, or a cytokine. A bioactive agent that is a nucleic acid may be for example single stranded or double stranded DNA or RNA, a short hairpin RNA, an siRNA, or may comprise a gene encoding a therapeutic product. Also included in the scope of bioactive agent are antibiotics, chemotherapeutic agents, antihypertensive agents, anti-cancer agents, anti-bacterial agents, anti-neoplastic agents, anti-thrombotic agents, vasodilatory agents, anti-oxidants, anti-mutagenic agents, anti-carcinogenic agents, anti-hypercholesterolemic agents, anti-viral agents and anti-inflammatory agents.

The bioactive agent may be added to the hydrogel solution before gelation of the hydrogel or may be injected along with the other components of the hydrogel such that the bioactive agent is incorporated in the hydrogel when the hydrogel forms in vivo. The bioactive agent may be included in the flavonoid conjugate hydrogel to be simultaneously delivered to a cell or to a target site in the body.

If an anti-cancer agent is included in the flavonoid conjugate gel, therapeutic synergism may be provided by the combination of the EGCG when delivered in combination with anti-cancer agents [13]. Thus, in one embodiment, the bioactive agent is an anti-cancer agent. As used herein, "anti-cancer agent" refers to any agent that has an anti-cancer effect on a cell, including an anti-tumour effect, such as a cytotoxic, apoptotic, anti-mitotic anti-angiogenesis or inhibition of metastasis effect. The anti-cancer effect is intended to include inhibition or reduction of tumour cell growth, inhibition or reduction of carcinogenesis, killing of tumour cells, or inhibition or reduction of carcinogenic or tumourogenic properties of a cell, including a tumour cell. The anti-cancer agent may be, for example, herceptin, TNP470, trastuzumab, bevacizumab, rituximab, erlotinib, daunorubicin, doxorubicin, etoposide, vinblastine, vincristine, pacitaxel, methotrexate, 5-fluorouracil, gemcitabine, arabinosylcytosine, altretamine, asparaginase, bleomycin, capecitabine, carboplatin, carmustine, BCNU, cladribine, cisplatin, cyclophosphamide, cytarabine, dacarbazine, dactinomycin, actinomycin D, docetaxel, doxorubicin, doxorubicin, imatinib, doxorubicin liposomal, VP-16, fludarabine, gemcitabine, hydroxyurea, idarubicin, ifosfamide, irinotecan, CPT-11, methotrexate, mitomycin, mitotane, mitoxantrone, topotecan, vinblastine, vincristine or vinorelbine or an antibody for use in immunotherapy.

The combination of the presently provided flavonoid conjugate hydrogel with a bioactive anti-cancer agent may have a synergistic anti-cancer effect greater than the combined effects of each of the flavonoid conjugate hydrogel and the bioactive anti-cancer agent when used alone. In one embodiment, the anti-cancer agent herceptin may be incorporated into the presently provided flavonoid conjugate hydrogel to provide a synergistic anti-cancer effect.

In particular embodiments, the present methods for forming a flavonoid conjugate hydrogel may comprise more than one type of flavonoid conjugate. Thus, in different embodiments, the hydrogel formed by the present methods may comprise a mixture of two or more types of flavonoid conjugates wherein each type of flavonoid conjugate comprises a different combination of a hydrogel forming agent and a flavonoid. For example, in one embodiment, the hydrogel may comprise a mixture of different types of flavonoid conjugates wherein each type of flavonoid conjugate comprises a different hydrogel forming agent. In another embodiment, the hydrogel may comprise a mixture of different types of flavonoid conjugates wherein each type of flavonoid conjugate comprises a different flavonoid. In yet another embodiment, the hydrogel may comprise a mixture of different types of flavonoid conjugates wherein each type of flavonoid conjugate comprises a different hydrogel forming agent and a different suitable flavonoid. In a particular embodiment, the hydrogel may comprise a mixture of HA-EGCG conjugates and a different type of flavonoid conjugate.

The mechanical strength of the presently described flavonoid conjugate hydrogels can be modified by varying the concentration of the flavonoid conjugates and the pH of the hydrogel. In one embodiment, the mechanical strength of the presently described hydrogel may be modified by varying the concentration of the flavonoid conjugates between from about 0.1 wt % to about 20 wt % and varying the pH of the hydrogel between from about 3 to about 10. In a particular embodiment, the mechanical strength of the presently described hydrogel may be modified by varying the pH of the hydrogel between from about 6 to about 8. A skilled person would be readily able to adjust the concentration of the flavonoid conjugate and the pH of the hydrogel, within the ranges described herein, to achieve a desired mechanical strength, for example, a particular mechanical strength to suit a particular application for the hydrogel.

Methods of Use of the Hydrogel

The enzymatically cross-linked flavonoid conjugate hydrogel described herein can is capable of adhesion of cells. Thus, there is presently provided a method for adhering a cell to a hydrogel, the method comprising contacting the cell with the enzymatically cross-linked flavonoid conjugate hydrogel described herein.

Use of the presently described enzymatically cross-linked flavonoid conjugate hydrogel to adhere a cell is also provided.

The enzymatically cross-linked flavonoid conjugate hydrogel may be selected to provide a desired effect on the adhered cells. For example, the concentrations of the components used to make the hydrogel may conveniently be selected to provide inhibition of proliferation of a cancer cell. As discussed above, cell adhesion to the enzymatically cross-linked flavonoid conjugate hydrogel described herein may provide improved delivery of flavonoids to a cell. In addition to delivery of flavonoids to a cell by sustained release of the flavonoid into a target site where cells are generally located, the presently described enzymatically cross-linked flavonoid conjugate hydrogel may facilitate delivery of flavonoids and other active agents in the hydrogel to a cell by adhering or "trapping" cells. That is, as a result of cell adhesion, the presently described enzymatically cross-linked flavonoid conjugate hydrogels may retain cells on the hydrogel and thus in proximity to the therapeutic agents contained in the hydrogel. Thus, the present enzymatically cross-linked flavonoid conjugate hydrogels may provide additional and potentially more efficient delivery of flavonoids and other active agents to cells than hydrogels to which cells do not adhere. In addition, the enzymatically cross-linked flavonoid conjugate hydrogel presently described may provide anti-metastatic effects.

FIG. 1 provides a schematic diagram of the potential biological activity of the enzymatically cross-linked flavonoid conjugate hydrogel presently described.

Thus, in one embodiment, the cell adhered to the enzymatically cross-linked flavonoid conjugate hydrogel is a cancer cell and proliferation of the cancer cells in inhibited.

In particular embodiments, the cell may be a cell located in a subject in need of treatment for cancer. For example, the cell may be a cell within a subject having cancer, a subject requiring treatment for cancer or a subject in which prevention of cancer is desired. In some embodiments, the subject is a human subject.

In another embodiment, the flavonoid conjugate hydrogel may be selected to have a sufficient amount of enzymatic cross-linking to allow for proliferation of a non-cancer cell. Thus, in one embodiment, the cell adhered to the enzymatically cross-linked flavonoid conjugate hydrogel is a non-cancer cell and the non-cancer cell is proliferated.

As used herein, "cancer cell" refers to a cell that exhibits abnormal cell growth, reduced or loss of control over cell division and the potential to invade nearby tissues. Some cancer cells may display metastasis in which the cell spreads to other locations in the body. Some cancer cells may form tumours. Cancer cells may include, for example, sarcoma, carcinoma, lymphoma or blastoma cells.

The term "non-cancer cell" as used herein refers to a cell that is not a cancer cell. A non-cancer cell is a cell that does not exhibit reduced or loss of control of cell division and the potential to invade nearby tissues. A non-cancer cell may include for example, a cell with normal cell growth and function, a cell with normal cell growth but abnormal cell function or a cell with abnormal cell growth that is not related to reduced or loss of control of cell division, for example a cell with reduced cell growth or abnormal cell morphology.

As used herein, the term "proliferation" and "proliferating" refers to the growth and division of a cell.

As used herein, "inhibiting proliferation" or "inhibition of proliferation" refers to a temporary or permanent decrease, slowing, inhibition, or termination in the proliferation of cells. For example, inhibiting proliferation may refer to suppressing cell growth and cell division by reducing, inhibiting or modifying cell development and function. Inhibiting proliferation may induce cell senescence or cell death, for example through inducing apoptosis.

As used herein, "selective anti-proliferative effect" refers to an inhibition of proliferation that affects cancer cells but does not affect non-cancer cells or affects non-cancer cells to a lesser degree.

The presently described enzymatically cross-linked flavonoid conjugate hydrogel may induce a selective anti-proliferative effect in cancer cells that adhere to the hydrogel while permitting the proliferation of adherent non-cancer cells adhered to the hydrogel. For example, an enzymatically cross-linked HA-EGCG hydrogel prepared as described herein did not induce any significant cytotoxicity against attached non-cancer cells, but inhibited cell proliferation and induced apoptosis of attached cancer cells. Thus, in one embodiment, the flavonoid conjugate hydrogel may be selected to have a sufficient amount of enzyme-catalyzed cross-linking to allow for proliferation of a non-cancer cell while at the same time having a selective anti-proliferative effect in a cancer cell that may be present in the same cell population as the non-cancer cell, including within a subject in need of cancer treatment.

In another embodiment, there is presently provided a method for delivering a flavonoid to a cell, the method comprising contacting the auto-oxidation flavonoid conjugate hydrogel described herein with the cell.

As used herein, "delivering" the flavonoid to a cell refers to providing the flavonoid in sufficiently close proximity to the cell such that the flavonoid can exert its therapeutic effects on the cell. In vitro, for example, the flavonoid may be delivered to the cell by adding the hydrogel to the cell culture media or using the hydrogel as a support for cell attachment and growth.

In particular embodiments, the method of adhering a cell to a hydrogel, described herein, or the method for delivering a flavonoid to a cell, described herein, may comprise administering to a subject flavonoid conjugate hydrogels comprising an effective amount of the conjugates for the treatment of disease or disorder, including, for example, cancer.

In vivo, the flavonoid conjugate hydrogels presently provided may be administered to a subject by any suitable manner of administration known in the art. For example, the hydrogel may be administered by topical application or by surgical insertion, including at a wound site or at a site for cancer treatment. In one embodiment, the components of the hydrogel, including a mixture of the components, may be administered by injection at the desired target site where the components will react to form the hydrogel in vivo.

The term "effective amount" as used herein means an amount effective at dosages and for periods of time necessary to achieve a desired result. For example, the flavonoid conjugates may be administered in quantities and dosages necessary to deliver a flavonoid which may function to alleviate, improve, mitigate, ameliorate, stabilize, prevent the spread of, slow or delay the progression of or cure a disease or disorder, or to inhibit, reduce or impair the activity of a disease-related enzyme. A disease-related enzyme is an enzyme involved in a metabolic or biochemical pathway, which when the pathway is interrupted, or when regulatory control of the enzyme or pathway is interrupted or inhibited, the activity of the enzyme is involved in the onset or progression of a disease or disorder, for example, cancer. In another example, the flavonoid conjugates may be administered in quantities and dosages necessary for inducing a selective anti-proliferative effect in a cancer cell adhered to the hydrogel while permitting proliferation of non-cancer cells on the hydrogel. In another example, the flavonoid conjugates may be administered in quantities and dosages necessary for exerting an anti-metastatic effect on a tumour. In yet another example, the flavonoid conjugates may be administered in quantities and dosages necessary for the treatment of cancer.

"Cancer" as used herein encompasses a class of diseases in which cells exhibit abnormal cell growth and the potential to invade nearby tissues. In some forms of cancer, the abnormal cells may also spread to other locations in the body. Different types of cancer include for example, breast cancer, colorectal cancer, brain cancer, prostate cancer, cervical cancer, ovarian cancer, bone cancer, skin cancer, lung cancer, pancreatic cancer, bladder cancer, gallbladder cancer, kidney cancer, esophageal cancer, Hodgkin lymphoma, non-Hodgkin lymphoma, laryngeal cancer, leukemia, multiple myeloma, oral cancer, pleural mesothelioma, small intestine cancer, testicular cancer, uterine cancer, thyroid cancer and stomach cancer.

The term "treatment" refers to an approach for obtaining beneficial or desired results, including clinical results. Beneficial or desired clinical results can include, but are not limited to, alleviation or amelioration of one or more symptoms or conditions, diminishment of extent of disorder or disease, stabilization of the state of disease, prevention of development of disorder or disease, prevention of spread of disorder or disease, delay or slowing of disorder or disease progression, delay or slowing of disorder or disease onset, amelioration or palliation of the disorder or disease state, and remission, whether partial or total. "Treatment" can also mean prolonging survival of a subject beyond that expected in the absence of treatment. "Treatment" can also mean inhibiting the progression of disorder or disease, slowing the progression of disorder or disease temporarily, although in some instances, it involves halting the progression of the disorder or disease permanently.

The effective amount of flavonoid conjugates to be administered to a subject can vary depending on many factors such as the pharmacodynamic properties of the flavonoid conjugates or the hydrogel comprising the flavonoid conjugates, including any bioactive agent incorporated in the hydrogel, the mode of administration, the age, health and weight of the subject, the nature and extent of the disorder or disease state, the frequency of the treatment and the type of concurrent treatment, if any, and the concentration and form of the hydrogel.

Furthermore, the effective amount may vary depending on the degree of enzymatic cross-linking of the flavonoid conjugates. For example, varying the degree of enzymatic cross-linking in the enzymatically cross-linked flavonoid conjugate hydrogel described herein may result in differences in the amount or strength of cell adhesion and thus may affect the efficiency of delivery of therapeutic agents to the cells.

One of skill in the art can determine the appropriate amount based on the above factors. The conjugate may be administered initially in a suitable amount that may be adjusted as required, depending on the clinical response of the subject. The effective amount of conjugate can be determined empirically and depends on the maximal amount of the conjugate that can be administered safely. However, the amount of conjugate administered is preferably the minimal amount that produces the desired result.

Therefore, there is provided a pharmaceutical composition comprising a flavonoid conjugate hydrogel as described herein. The pharmaceutical composition may further include a pharmaceutically acceptable diluent or carrier. The pharmaceutical composition may routinely contain pharmaceutically acceptable concentration of salts, buffering agents, preservatives and various compatible carriers. For all forms of delivery, the flavonoid conjugate hydrogel may be formulated in a physiological salt solution.

The proportion and identity of the pharmaceutically acceptable diluent or carrier is determined by the chosen route of administration, compatibility with biologically active proteins if appropriate, and standard pharmaceutical practice.

The pharmaceutical composition can be prepared by known methods for the preparation of pharmaceutically acceptable compositions suitable for administration to subjects, such that an effective amount of the flavonoid conjugates and any additional active substance or substances is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions may include the flavonoid conjugate hydrogel in association with one or more pharmaceutically acceptable vehicles or diluents, and contained in buffer solutions with a suitable pH and iso-osmotic with physiological fluids.

Under ordinary conditions of storage and use, such pharmaceutical compositions may contain a preservative to prevent the growth of microorganisms, and that will maintain any biological activity of the flavonoid conjugate hydrogel. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999. Alternatively, the flavonoid conjugate hydrogel may be formulated at a time sufficiently close to use by mixing the components, without the need for preservatives.

The term "cell" as used herein includes a single cell, a plurality of cells or a population of cells where context permits, unless otherwise specified. The cell may be an in vitro cell, including a cell explanted from a subject. The cell may be a cell grown in batch culture or in tissue culture plates. Alternatively, the cell may be an in vivo cell in a subject. In some embodiments, the subject is a human subject. Similarly, reference to "cells" also includes reference to a single cell where context permits, unless otherwise specified.

The term "stem cell" as used herein refers to an undifferentiated cell that is capable of indefinite cell renewal and differentiation into a variety of cell types or a precursor cell that is partially differentiated along a particular cell lineage and for which further differentiation is restricted to cells of that particular lineage. The stem cell may be any type of stem cell, including an embryonic stem cell or an adult stem cell, including for example a mesenchymal stem cell.

Also presently provided is a hydrogel for adhering a cell, comprising conjugates of a hydrogel forming agent and a flavonoid wherein said conjugates are enzymatically cross-linked for adhesion of the cell to the hydrogel. In one embodiment, the hydrogel is a hydrogel formed by the methods disclosed herein.

The present methods and hydrogels are further exemplified by way of the following non-limiting examples.

EXAMPLES

Example 1

Materials and Methods

Materials: Hyaluronic acid (HA, 90 KDa) was kindly donated by Chisso Corporation (Tokyo, Japan). 1-Ethyl-3-(3-dimethylaminopropyl)-carbodiimide hydrochloride (EDC.HCl) and N-hydroxysuccinimide (NHS) was purchased from Sigma-Aldrich (Singapore). Hydrogen peroxide ($H_2O_2$) was obtained from Lancaster. Horseradish peroxidase (HRP, 100 units/mg) was purchased from Wako Pure Chemical Industries (Japan). DMEM media was obtained from Sigma-Aldrich (Singapore). 4',6-Diamidino-2-phenylindole, dihydrochloride (DAPI), and cell culture supplements were obtained from Gibco (Invitrogen Singapore). Fetal bovine serum (FBS) was purchased from Hyclone (Research Instrument, Singapore). Penicillin and streptomycin were obtained from JRH biosciences (Singapore). AlamarBlue® was purchased from TREK Diagnostic Systems (England). Other general use chemicals were purchased from Sigma-Aldrich (Singapore). BD BioCoat Matrigel™ invasion chambers and cell culture inserts were purchased from BD Bioscience (USA). Unless stated otherwise, all reagents and solvents were of biological grade, and were used without further purification.

Synthesis of HA-diethylaminoacetal (HA-AA) conjugate: HA (5 g, 12.5 mmol, Mw 90K) was added to 500 ml deionized water and allowed to dissolve by vigorous stirring. Aminoacetaldehyde diethyl acetal (1.19 g, 9.0 mmol, Sigma-Aldrich), NHS (1.16 g, 14 mmol) and EDC HCl (2.395 g, 12.5 mmol, Sigma-Aldrich) were added and the pH of the solution was adjusted to 4.7. The resulting solution was stirred overnight under ambient conditions. The solution was then adjusted to pH 7 with 10M NaOH. The synthesized product was first dialyzed against 100 mM NaCl solution for two days, followed by dialysis in 25% v/v ethanol in deionized water for two days, and deionized water for two days using a dialysis tubing (Spectrapore®7 membrane, MWCO=3500). Purified HA-AA was lyophilized. The degree of substitution (the number of diethylaminoacetal molecules per 100 repeating units of HA) was calculated from $^1$H NMR measurement by comparing the ratio of the relative peak integrations of methyl proton of diethylaminoacetal (peak at 0.99-1.04 ppm) and methyl proton of HA (1.93 ppm). The degree of substitution was 12. $^1$H NMR ($D_2O$): δ 0.99-1.04 (m, 6H methyl of diethyl acetal), 1.829 (3H, N-acetyl), 3.10-3.70 (14H from HA part and 4 H from the ethyl groups of AA, five broad signals), 4.10-4.40 (2H, HA protons from the acetamide and acid group bearing carbons), 4.465 (2H, proton attached to the acetal carbon, disappears upon deprotection).

Synthesis of HA-EGCG conjugates: HA-AA (712 mg, 1.83 mmol HA units, 0.216 mmol acetal units) was dissolved in deionized water (40 mL) and degassed by bubbling nitrogen through the solution. In a separate flask, epigallocatechin gallate (EGCG, 1 g, 2.18 mmol, 10.09 equivalents with respect to the acetal units) was added to 8 ml of degassed DMSO, and allowed to dissolve by stirring at room temperature. The DMSO solution of EGCG was then mixed with the solution of HA-AA under nitrogen atmosphere, the pH of the solution was adjusted to pH 1 using concentrated HCl while bubbling with nitrogen. The reaction was allowed to occur at room temperature for 24 h. The resulting solution was dialyzed against degassed deionized water for 3 days, followed by lyophilization.

Synthesis of enzymatically cross-linked HA-EGCG hydrogel: 1 μl of $H_2O_2$ solution (1.42 mmol/l) and HRP solution (25 units/ml) at various volume (0 to 25 μl) were added sequentially to a well of 96-well cell culture plate. To this 100 μl of HA-EGCG (20 mg/ml), Dulbecco's Modified Eagle's Medium (DMEM) solution containing 10% fetal bovine serum (FBS) was added and stirred vigorously with a pipette tip. The enzyme mediated oxidation reaction of HA-EGCG was allowed to proceed for 24 h inside a cell culture hood. Enzymatically cross-linked hyaluronic acid-tyramine (HA-Tyr) hydrogel, gelatin-(hydroxyphenyl)propionic acid (Gtn-HPA) hydrogel, and HA-Tyr/Gtn-HPA hydrogel were employed as controls in this study. HA-Tyr hydrogel and Gtn-HPA hydrogels were prepared as described previously [4, 15, 16]. HA-Tyr/Gtn-HPA mixed hydrogel were prepared by simple mixing of HA-Tyr and Gtn-HPA polymer at various mass ratio, followed by oxidative coupling of tyramine or (hydroxyphenyl)propionic acid moieties catalyzed by hydrogen peroxide ($H_2O_2$)

Cell Culture, Cell Adhesion and Cell Image Analysis: Human Foreskin fibroblast cells (HFF-1), human fibrosarcoma (HT-1080), and human hepatocellular carcinoma cells (Hep G2) were purchased from American Type Culture Collection (ATCC, USA). Cells were grown and maintained in DMEM supplemented with 10% FBS, 2 mM L-glutamine, and 50 units/ml penicillin streptomycin at 37° C. in a humidified 5% carbon dioxide incubator. Cells were seeded at a density of $2\times10^4$ per well in 96-well plates coated with hydrogel and incubated for the indicated time period at 37° C. Non-adherent cells were removed by rinsing with PBS. The surface of the gel was examined after 24-144 h of incubation using an Olympus IX71 light microscope attached to a video camera. Image analysis of projected cell area was performed with Image-Pro® Plus (MediaCybernetics, USA). The projected cell area measurement was obtained by tracing cell boundaries, and this parameter is displayed as an average (±standard error of mean).

Cell proliferation on the surface of hydrogels: Hep G2 and HFF-1 cells were seeded at $2 \times 10^4$ cells per well in 96-well plates coated with 100 µl HA-EGCG or HA-Try/Gtn-HPA (80:20, w/w) hydrogels each cross-linked by 1 µl of $H_2O_2$ (1.42 mmol/l) and 25 µl HRP solution (25 units/rill). The proliferations of cells were evaluated in terms of AlamarBlue® reduction using AlamarBlue® assay. After 24-96 h incubation, spent media were replaced with fresh complete media containing 10% AlamarBlue®, and cultured for another 4 h. The cells seeded on HA-Tyr/Gtn-HPA (80:20 w/w) hydrogel were used as control. Hydrogel substrates without any cells were used as blank controls. The absorbance values were recorded on a microplate reader (GENios Pro, Tecan, Austria) with wavelength at 570 nm and 600 nm.

DNA fragmentation assay: After 120 h of incubation, cells cultured on the hydrogel surface were washed twice with phosphate-buffered saline (PBS) and then fixed by 4% paraformaldehyde for 30 min. The cells were rinsed with PBS, followed by incubation in a 1 µg/ml DAPI nucleic acid stain for 30 min in the dark. The cells were rinsed again and observed by a fluorescence microscope (Olympus, Tokyo, Japan).

Cancer cell invasion assay: HA-EGCG hydrogels were prepared by adding 20 µl of HA-EGCG solution on cell culture inserts with 8 µm pore size. HT-1080 were ($2.5 \times 10^4$ cells/well) added to the upper compartment of the invasion chamber. Culture medium was added to the lower compartment of the invasion chamber. The chambers were incubated at 37° C. in a humidified 5% carbon dioxide incubator and cells were allowed to migrate for 90 h. Matrigel™ coated (filter inserts with 8.0 µm pore size) invasion chambers were used as a control. After incubation, the membrane inserts were removed from the wells, cells on the upper side of the membrane were removed using cotton swabs. The membranes were fixed, stained, and mounted according to the manufacturer's instructions.

Animal study: Tumour growth inhibition of human breast BT474 cancer in Mice was examined. Mice with human breast BT474 cancer were treated with either a control phosphate buffered saline solution (PBS), a HA-EGCG hydrogel (formed using 2.5 µl of 25 units/ml of HRP), herceptin or a herceptin loaded HA-EGCG hydrogel. The HA-EGCG hydrogel and herceptin loaded HA-EGCG hydrogen were administered once subcutaneously. The herceptin was administered twice weekly intraperitoneally.

Materials: HA (90 KDa) was kindly donated by Chisso Corporation (Tokyo, Japan). Diethoxyethyl amine (DA), N-hydroxysuccinimide (NHS), 1-ethyl-3-(3-dimethylamino-propyl)-carbodiimide hydrochloride (EDC), dimethyl sulfoxide (DMSO), xanthine, sodium chloride (NaCl) and catalase from bovine liver were from Sigma (Singapore). Di-sodium hydrogen phosphate dihydrate and sodium dihydrogen phosphate monohydrate were obtained from Merck (Singapore). Horseradish peroxidase was purchased from was from Wako Pure Chemical Industries (Japan). Ethanol is purchased from Fisher Scientific (Singapore). EGCG (>95% purity) was purchased from Kurita Water Industries (Tokyo, Japan).

Synthesis of HA-DA conjugates: HA-DA conjugates were synthesized using a standard carbodiimide coupling method. Briefly, HA (5 g, 12.5 mmol) was dissolved in 500 ml of distilled water. To this diethoxyethyl amine (DA) with different amounts (1.19 g, 8.93 mmol or 2.38 g, 17.8 mmol) was added, followed by NHS (1.16 g, 10.0 mmol) and EDC (2.40 g, 12.5 mmol) to initiate the conjugation reaction. As the reaction proceeded, the pH of the mixture was maintained at 4.7. The reaction mixture was stirred overnight at room temperature after which the pH was increased to 7.0. The solution was transferred to dialysis tubes with a molecular cut-off of 1000 Da. The tubes were dialyzed against 100 mM NaCl solution for 2 days, a mixture of distilled water and ethanol (3:1) for 1 day and distilled water for 1 day, successively. The purified solution was lyophilized to obtain the HA-DA conjugate (4.2 g).

Synthesis of HA-EGCG conjugates. HA-DA conjugates with different substitution degrees (1 g) were dissolved in 57 ml of distilled water. The solution was then purged with nitrogen gas for 20 min. EGCG (25 equivalents of molar concentration with respect to the DA units) was dissolved in 23 ml of nitrogen purged DMSO and added to the solution of HA-DA conjugate. The pH of the solution was adjusted to 1.0 using concentrated HCl. The mixture was stirred at room temperature for 24 h under a nitrogen atmosphere. After which the solution was transferred to dialysis tubes with a molecular cut-off of 3500 Da and dialyzed against distilled water under nitrogen atmosphere for 3 days. The purified solution was lyophilized to obtain the HA-EGCG conjugate (0.87 g).

Preparation of Ha-EGCG Solution: for all experiments described below, HA-EGCG stock solution was prepared by dissolving the conjugates in distilled water at 25 mg/ml at room temperature using a magnetic stirrer. Dissolution took about 25 min and the pH of the solution was 2.5. Then the pH was brought to 6 using 2 M NaOH before diluting with sodium phosphate buffer (final ionic strength: 0.15 M) to the desired concentration and pH, depending on the gelation condition.

Formation of HA-EGCG hydrogels through air autoxidation: To form HA-EGCG hydrogel by air autoxidation, HA-EGCG solution was diluted to 17.5 mg/ml by adding sodium phosphate buffer with pH between 6.0 to 8. To determine the gelation time, glass vials containing 0.25 ml of HA-EGCG were tilted frequently at 90 degrees for 5 sec, the time at which no obvious flowing motion could be observed was recorded as the gelation time.

Acceleration of HA-EGCG hydrogel formation through air autoxidation by adding catalase: Stock solution of catalase was prepared by dissolving the enzyme in distilled water at 22.5 kU/ml. The final HA-EGCG concentration was 17.5 mg/ml at pH 7.4 and the catalase concentration ranged from 0 to 4 kU/ml. The gelation time was determined as described above.

Measurement of $H_2O_2$ production by HA-EGCG: The amount of $H_2O_2$ produced by HA-EGCG was determined using the PeroXOquant Quantitative Peroxide Assay Kits from Pierce. In order to determine the amount of $H_2O_2$ produced during the dissolution process, a sample of the dissolved conjugates was diluted 20-fold with distilled water, 20 µl of which was added to the well of a 96-wellplate follow by the addition of 200 µl working reagent prepared according to manufacturer's protocol. The HA-EGCG solution was then diluted to 10 mg/ml with phosphate buffer. The final ionic strength of the mixture was 0.15 M and pH was 7.4. For the next 35 min, 20 µl of the HA-EGCG solution was drawn out every 5 min and diluted 10-fold with distilled water. 20 µl of the diluted sample was then added to a well of a 96-wellplate followed by 200 µl of working reagents. After the last sample was collected and the working reagent added, the plate was incubated for another 1 h before reading the absorbance at 595 nm. The amount of $H_2O_2$ produced by HA-EGCG was determined by comparing to a set of $H_2O_2$ standards.

Formation of HA-EGCG hydrogel by HRP-mediated crosslinking reaction: HRP stock solution was prepared in water at 6.25 U/ml. The final HA-EGCG concentration was 17.5 mg/ml at pH 7.4 and the HRP concentration ranged from 0 to 0.13 U/ml. The gelation time was determined as described above.

Measurement of storage modulus (G') of HA-EGCG hydrogels: 500 ul of the HA-EGCG solution at different pH, or containing different concentration of catalase or HRP, were placed on top of a glass plate. The glass plate was covered with a thin later of Parafilm to prevent the hydrogel from sticking to the glass surface. A second plate, also Parafilm-coated, was then placed on top to sandwich the hydrogel within a 1.5 mm gap, forming a circular hydrogel slab with diameter of approximately 2 cm. The plates were then wrapped with cling wrap to prevent evaporation and the hydrogels were allowed to form at 37° C. in a humidified environment for 24 hrs. After which the hydrogels were removed and gently placed on the bottom plate of a plate-plate serrated sensor (PP20) in a HAKKE Rheoscope 1. The top plate was then lowered to a measurement gap of 0.9 to 1 mm. The measurement parameters were performed in controlled deformation mode of 0.1% at 0.1 Hz. Preliminary experiments were done to ensure that the measurement parameters were within the linear viscoelastic range of the hydrogels. Each reading was an average of four measurement cycles and the first four readings were averaged to give the G'.

Results

Figure 2:
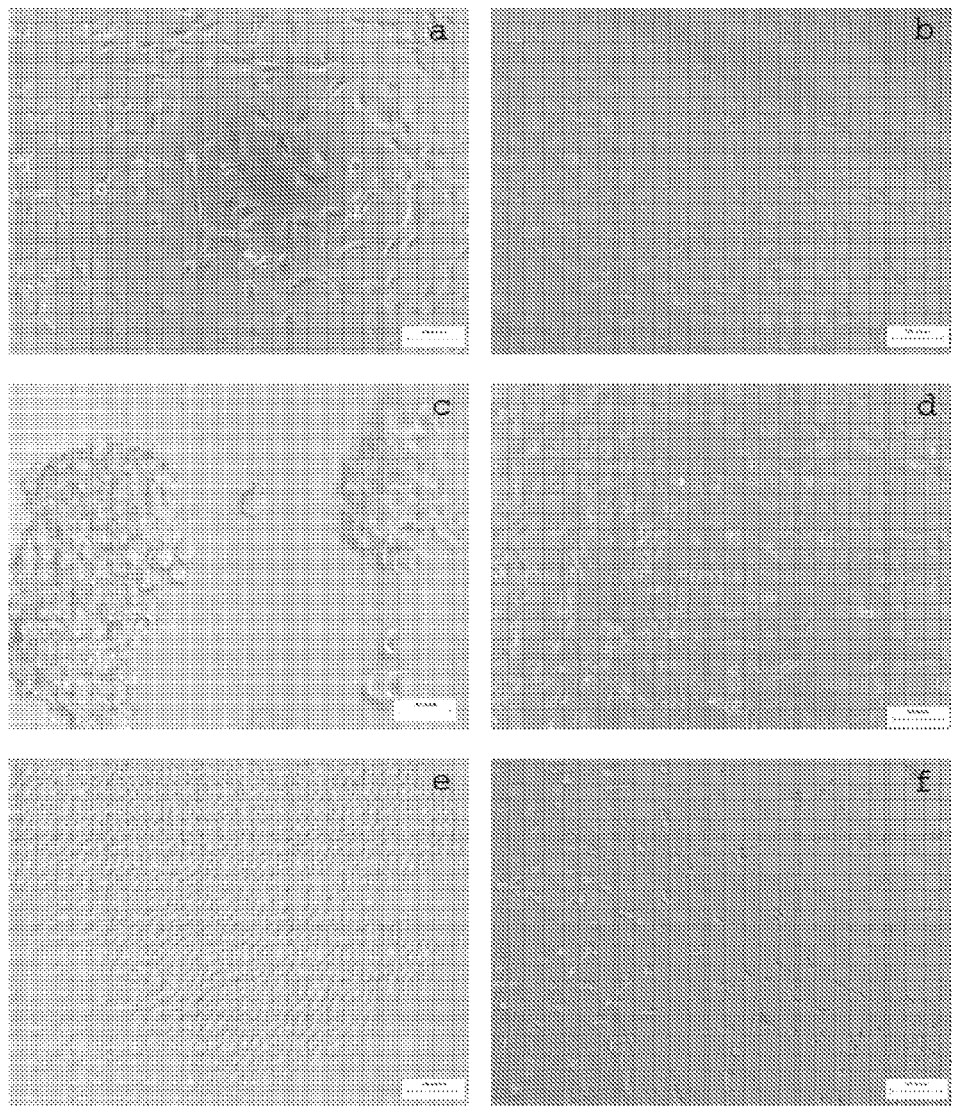
FIG. 2. Cell adhesion. HT-1080 cells cultured on (a) plastic well plate; (b) Gtn-HPA; (c) HA-Tyr; (d) HA-Tyr/Gtn-HPA (20:80 w/w); (e) oxygenic-cross-linked HA-EGCG; and (f) enzymatic cross-linked HA-EGCG.

Cell adhesion on HA-EGCG: In order to investigate whether HA-EGCG hydrogel can provide anchorage for cell attachment, adhesion assays were performed by seeding cells onto the surface of hydrogel. Representative photomicrographs of the HT-1080 cells cultured for 24 h on various hydrogels are shown in FIG. 2. It is well known that cells do not attach on HA-based hydrogel because cells adhesion is prevented by the hydrophilicity of hyaluronic acid [17, 18]. Some studies have showed improved cell attachment by conjugating RGD peptide, collagen or gelatin to HA-based hydrogels [19, 20]. In the present study, HA-Tyr hydrogel and HA-Tyr/Gtn-HPA (20:80 w/w) hydrogel were used as negative and positive control, respectively (FIGS. 2c and d). Cells were also seeded onto a plastic plate (FIG. 2a) and on a Gtn-HPA hydrogels (FIG. 2b) as controls. Cells attached to HA-Tyr/Gtn-HPA (80:20 w/w) hydrogel. It was observed that cells did adhere loosely to HA-Tyr, but never spread out and they could easily be detached by rinsing with PBS for assay. These results were consistent with other hyaluronan system [17, 18]. Interestingly, cells could be attached and uniformly spread out on the surface of HA-EGCG prepared by enzyme-mediated oxidation (FIG. 2f). However, similarly to the HA-Tyr hydrogel, cells only adhered loosely to HA-EGCG hydrogel prepared by oxygenic-oxidation (FIG. 2e).

These results provide evidence that the presence of the EGCG domain conferred the cell binding affinity to the HA-EGCG hydrogel. The differences in adhesiveness might be due to the difference in the cross-linked EGCGs structure. Under typical cell culture conditions, EGCG undergoes oxygenic-oxidation (known as auto-oxidation) to produce superoxide radicals and EGCG radicals with unpaired electrons delocalized around the B ring. A chain reaction is propagated by the reaction of superoxide with EGCG, generating EGCG dimers and $H_2O_2$ [9, 21]. The dimerization of EGCG results in cross-linking of HA-EGCG yielding hydrogel formation. In contrast, in the presence of HRP, the possible mechanistic pathway of enzymatic oxidation of HA-EGCG is proposed as follows: HRP catalyzes the decomposition of $H_2O_2$ at the expense of aromatic proton donors, leading to the coupling of phenols with $H_2O_2$ as an oxidant and resulting in the formation of oligomeric compounds consisting of phenylene and oxyphenylene units [22]. The hydrogel produce from enzymatically cross-linked HA-EGCG can consist of a complex mixture of EGCG dimers and EGCG oligomers. The HRP concentration play a role in determining the ratio of EGCG oligomers to dimers. The ratio of oligomers to dimers can be elevated by increasing the HRP concentration. Enzymatic oxidation is overwhelmingly faster than oxygenic oxidation and exhausting the supply of EGCG in enzymatic oligomerization can inhibit the oxygenic dimerization of EGCG. The ratio of EGCG oligomers to dimers can therefore be modulated by varying the HRP concentration. The results demonstrated that enzymatic cross-linked HA-EGCG hydrogel allowed cells to adhere and provided better anchorage for cell spreading compared to oxygenic-cross-linked HA-EGCG hydrogel. This data provided evidence that the strength of cell adhesion can be manipulated by varying the HRP concentration which controls the ratio of oligomers to dimers of EGCG produced during cross-linking.

Cell spreading responses: Cellular adhesion and integration with tissue is an important prerequisite for the design of tissue engineering constructs. HA-EGCG hydrogel has shown cellular adhesive properties as described earlier. It was important to further examine cellular activity on HA-EGCG. Cell functions such as spreading and proliferation are anchorage-dependent, and cell shape is affected by the extent of cell spreading. Cell spreading can be readily quantified by measuring its projected cell area and this parameter can also be used as an indicator for cell viability and proliferation. For example, cells such as fibroblasts typically exhibit spindle-shape morphology, the intermediate projected cell area is maximal with this morphology [23].

Quantification of the degree of dimerization or oligomerization in a HA-EGCG hydrogel remains a technical challenge, however, study of the relationship of HRP concentration and the physiological behaviour of cells provides insight into the structural importance of HA-EGCG. HT-1080 cells and Hep G2 cells were cultured on HA-EGCG hydrogels cross-linked by various amounts of HRP and the cell spreading behavior was examined. It has been reported that cell spreading is substrate-stiffness dependent [24, 25]. In order to minimize mechanical strength variation between hydrogels in this study, enzymatic-cross-linked hydrogel with similar gel stiffness were prepared by varying HRP concentration but fixing the $H_2O_2$ concentration.

Figure 3:
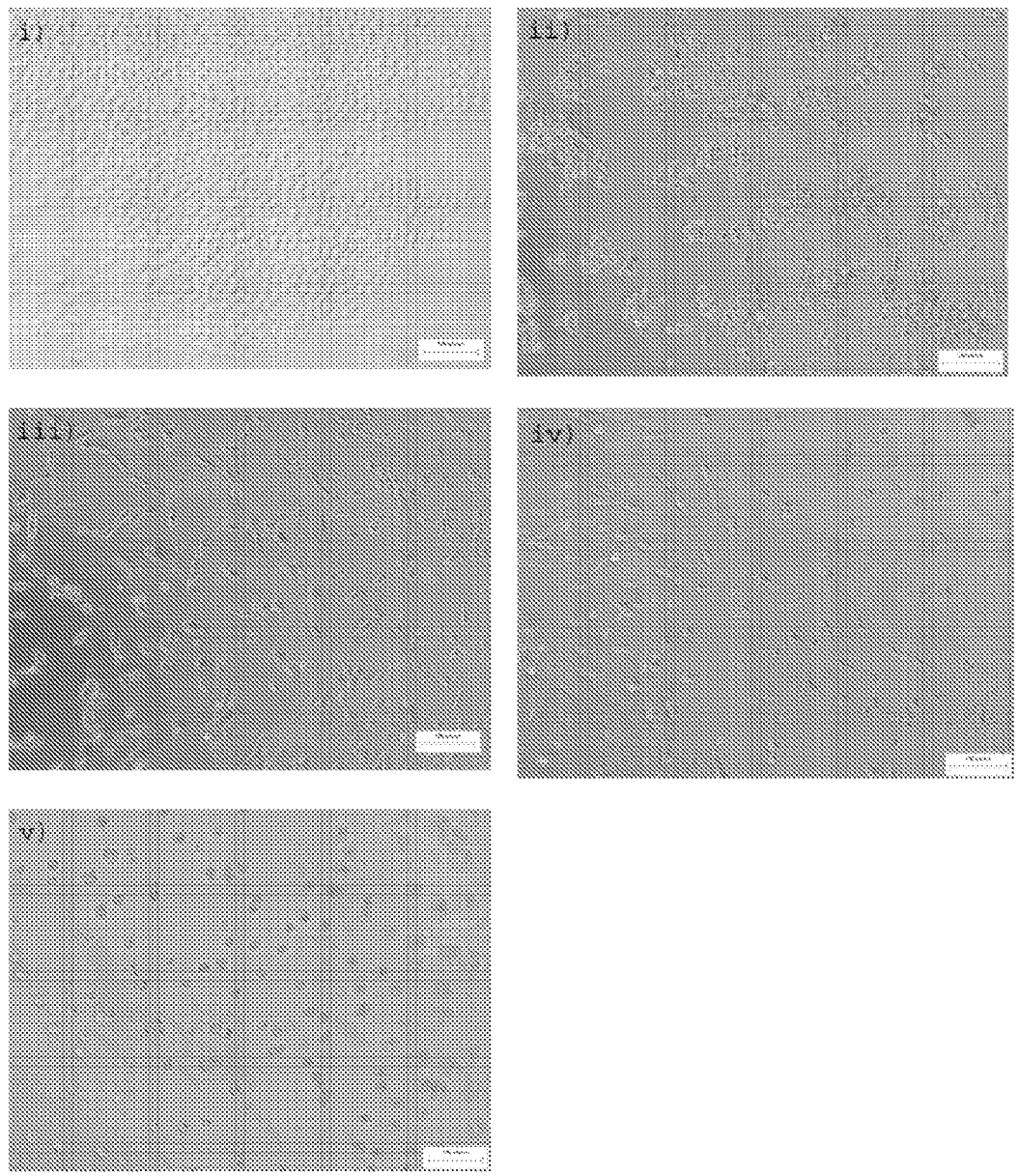
FIG. 3. The effect of HRP concentration on cell adhesion and spreading. (a) HT-1080 cells; and (b) HepG2 cells cultured on HA-EGCG hydrogel enzymatically cross-linked by (i) 0; (ii) 2.3; (iii) 3.2; (iv) 4.1; and (v) 4.9 units/ml of horse radish peroxidase (HRP).
Figure 3:
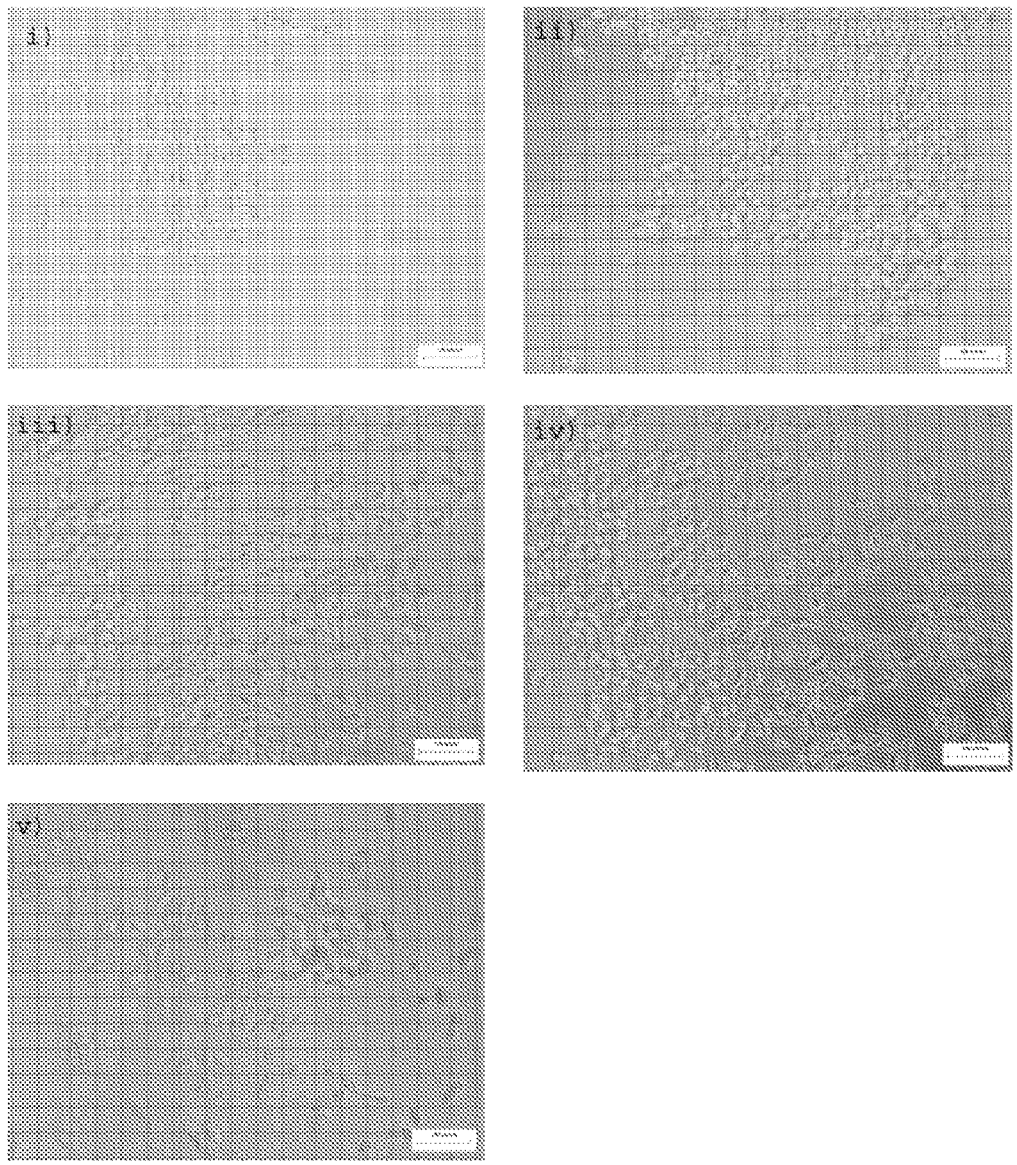

Representative photomicrographs of HT-1080 and Hep G2 cells are shown in FIG. 3a and FIG. 3b respectively. Cell spreading was remarkably dependent on the amount of HRP used for HA-EGCG gel formation. Concentrations of 0 units/ml (FIG. 3a (i) and FIG. 3b (i)), 2.3 units/ml (FIG. 3a (ii) and FIG. 3b (ii)), 3.2 units/ml (FIG. 3a (iii) and FIG. 3b (iii)), 4.1 units/m (FIG. 3a (iv) and FIG. 3b (iv)), and 4.9 units/ml ((FIG. 3a (v) and FIG. 3b (v)). The cell attachment was greater and the cells were more uniformly spread on enzymatically cross-linked HA-EGCG than oxygenic-cross-linked HA-EGCG, implying cells responded to different structure of HA-EGCG. The images also showed the tendency of cells to extend projections.

Figure 4:
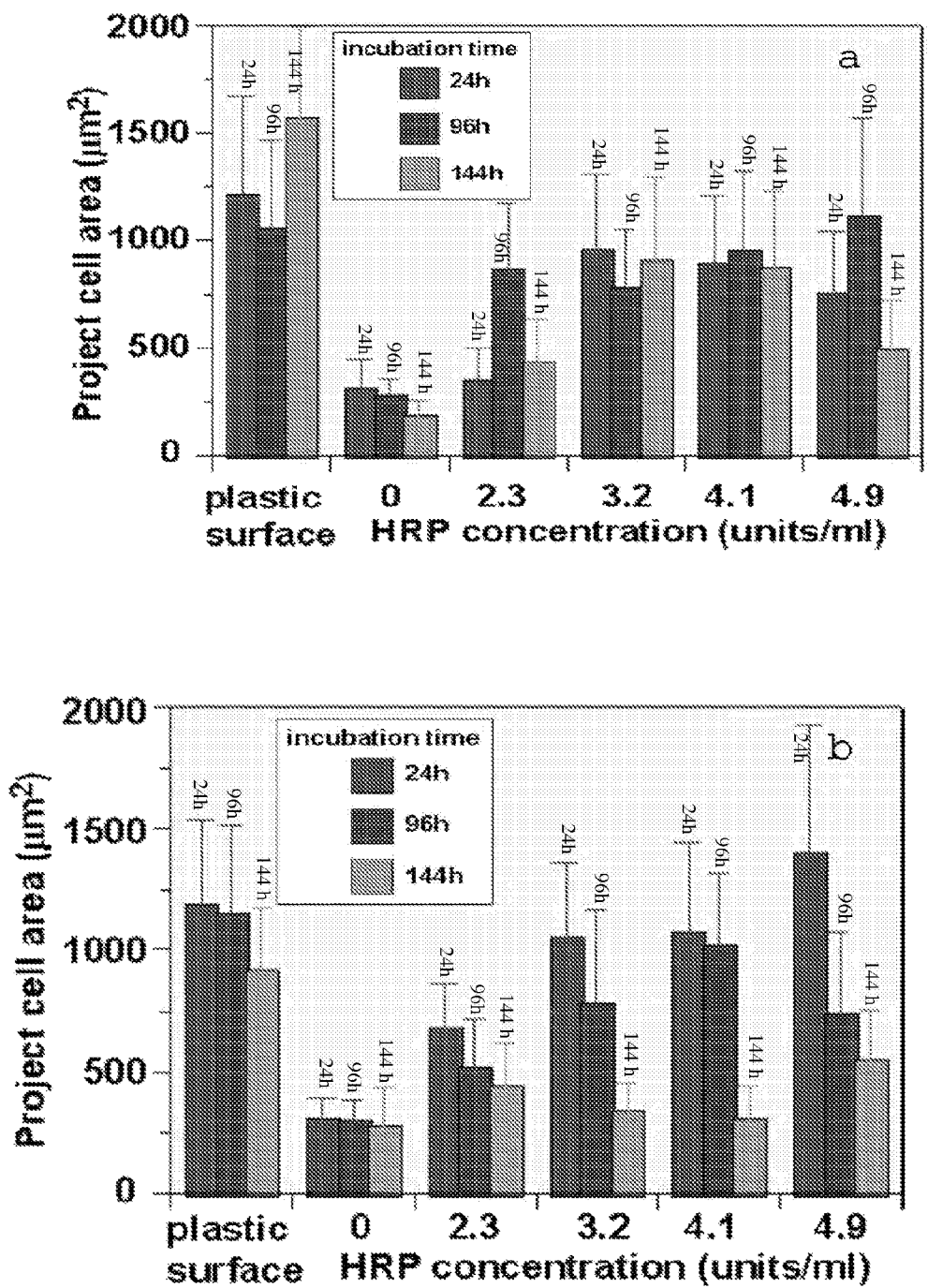
FIG. 4. Cell spreading. Cell morphology was analyzed on the projected cell area as a function of HRP concentration in substrate after 24 h, 96 h and 144 h incubation. Cell spreading of (a) HT-1080; (b) Hep G2; and (c) HFF-1 on enzymatically cross-linked HA-EGCG hydrogel. Cells cultured on plastic well plate were used as a control.
Figure 4:
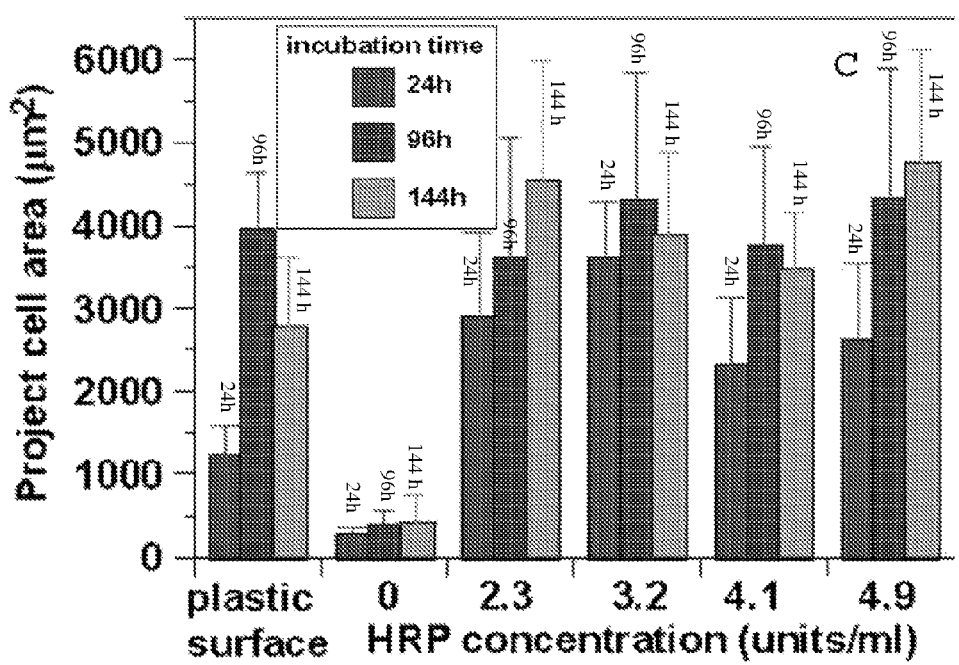

Cell spreading was further quantified by projected cell area measurement as illustrated in FIG. 4a-c. After 24 h incubation, the projected cell areas of HT-1080, Hep G2, and HFF-1 cells cultured on enzymatically cross-linked hydrogel were larger than those cultured on oxygenic-cross-linked hydrogel. FIG. 4a demonstrates the trend of projected cell area of HT-1080 cells which increased with increasing HRP concentration and became steady as the concentration of HRP reached 3.2 unit/ml, where the projected cell area reached a maximum (similar to cells cultured on a plastic well). For the case of Hep G2 cells, the projected cell area increased with increasing HRP concentration until it reached the maximum (FIG. 4b). The systematic increase in the extent of cell spreading could be due to increasing density of adhesive domains presented on the hydrogel. HA-EGCG hydrogel cross-linked with higher HRP concentration might present more adhesive domains than HA-EGCG cross-linked with lower HRP concentration.

After 96-144 h, a pronounced difference in projected cell area was found, where cells cultured on oxygenic-cross-linked HA-EGCG hydrogel still remained in spherical shape, as compared to spread cells adhered to enzymatically-cross-linked HA-EGCG hydrogel. As revealed by the projected cell area in FIG. 4c, HFF-1 cells remain viable and spread in similar manner as cells cultured on plastic well-plate. It is interesting to note that, on the other hand, the projected cell areas of HT-1080 and Hep G2 cells decreased (FIGS. 4a & 4b). The decrease in the extent of cell spreading could be due to a decrease in cell viability, where HA-EGCG exerts an anti-proliferative effect on cancer cells. As shown in FIG. 4b, the decrease in Hep G2 projected cell area seems to be HRP dependent. This data provides further evidence that cell adhesion to and bioactivity of HA-EGCG is related to the cross-linked structure of EGCG.

Cell proliferation and DNA fragmentation on HA-EGCG hydrogel: With regard to biocompatibility concerns, HA-EGCG hydrogel should exhibit minimal cytotoxicity to normal cells. To investigate the cytotoxic effect of HA-EGCG, the proliferation of HT-1080 and HFF-1 cells were examined by phase contrast microscopy and quantitatively using a colorimetric growth indicator based on detection of metabolic activity. As cells proliferate, innate metabolic activity results in a chemical reduction of AlamarBlue®, thus causing a change in colour. The amount of reduced AlamarBlue® was calculated based on the absorbance values obtained according to the manufacturer protocol.

Figure 5:
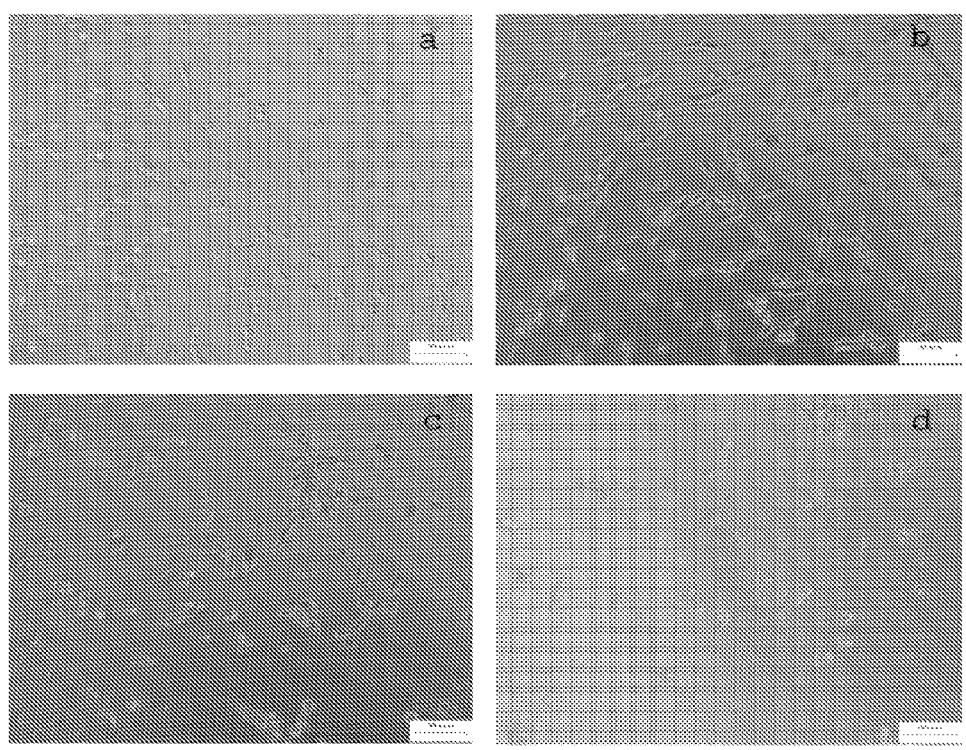
FIG. 5. Cell proliferation and morphology of HT-1080 cells. HT-1080 cells were cultured on HA-EGCG hydrogel cross-linked using HRP (4.1 units/ml) for the duration of (a) 24, (b) 48, (c) 96, and (d) 144 h. HA-EGCG hydrogel induced growth inhibition and the morphological change in HT-1080 cells. The morphology of cells was observed under phase-contrast microscopy with 200× power.
Figure 6:
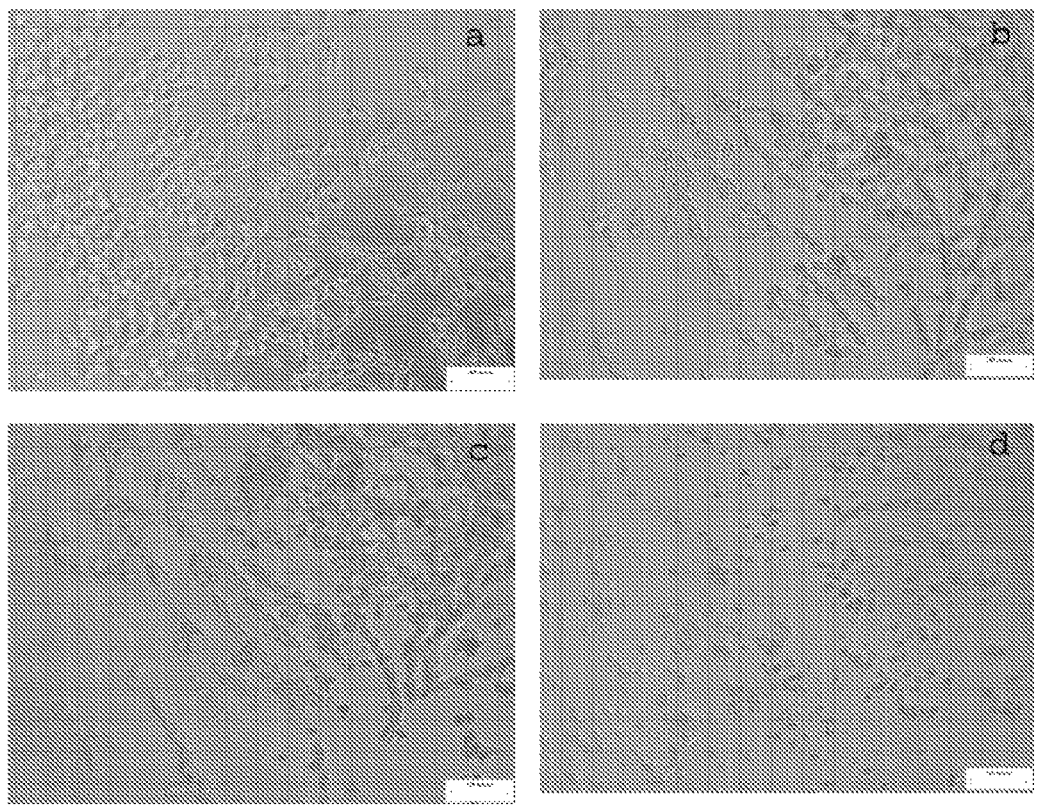
FIG. 6. Cell proliferation and morphology of Hep G2 cells. Hep G2 cells were cultured on HA-EGCG hydrogel cross-linked by HRP (4.1 units/ml) for the duration of (a) 24, (b) 48, (c) 96, and (d) 144 h. HA-EGCG hydrogel induced growth inhibition and the morphological change in Hep G2 cells. The morphology of cells was observed under phase-contrast microscopy with 200× power.
Figure 7:
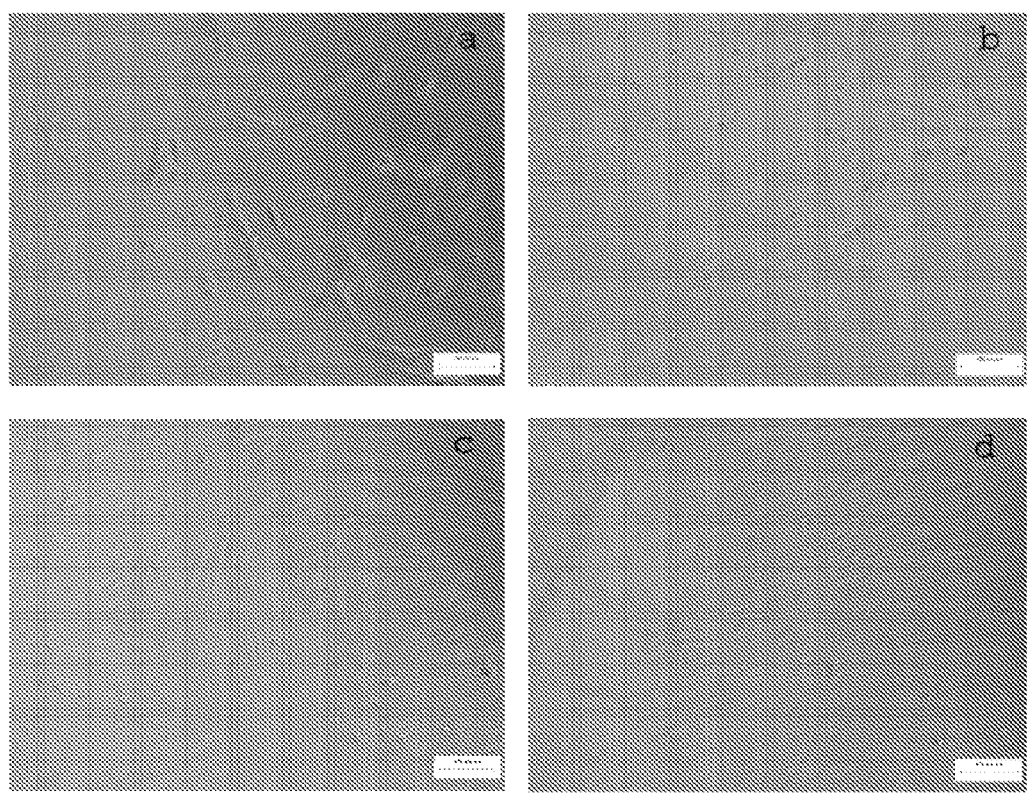
FIG. 7. Cell proliferation and morphology of HFF-1 cells. HFF-1 cells were cultured on HA-EGCG hydrogel cross-linked by HRP (4.1 units/ml) for the duration of (a) 24, (b) 48, (c) 96, and (d) 144 h. HA-EGCG hydrogel enables proliferation of human fibroblast cells. The morphology of cells was observed under phase-contrast microscopy with 200× power.
Figure 8:
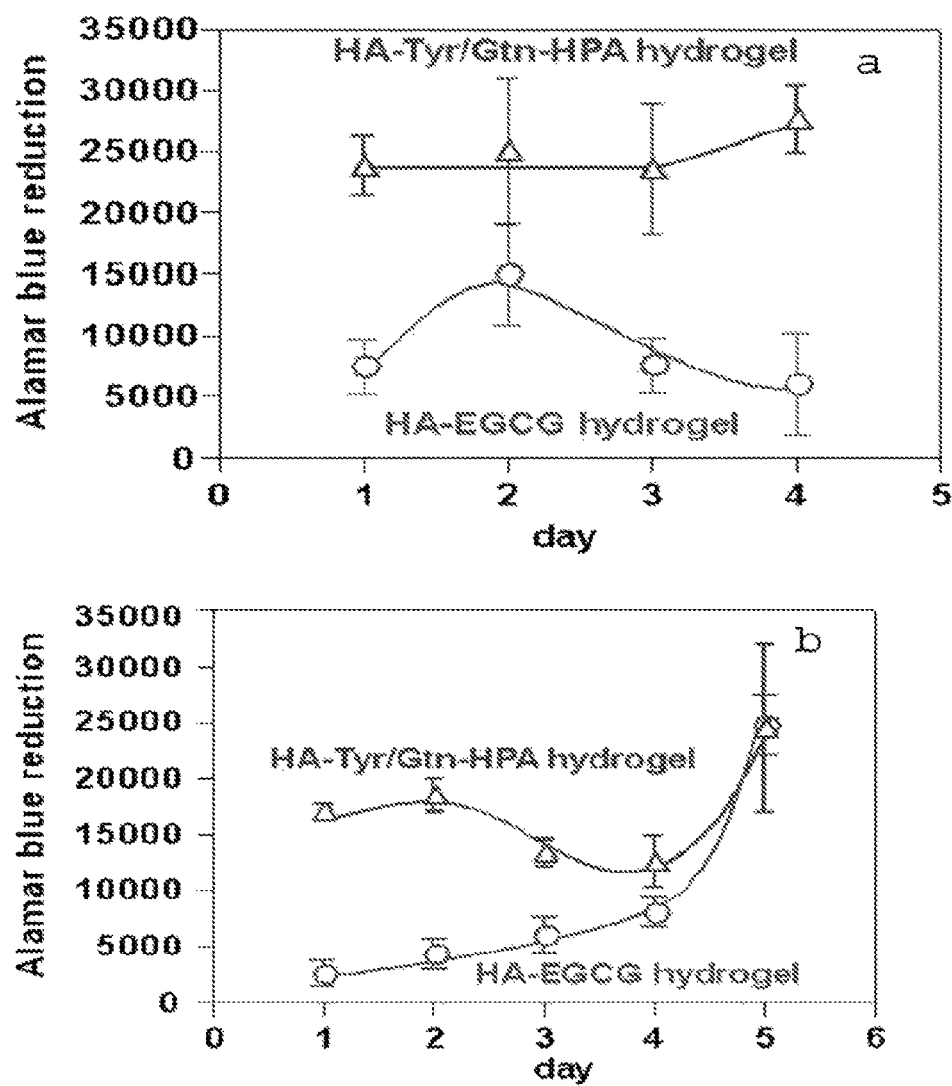
FIG. 8. AlamarBlue® assay for cell proliferation. Cell proliferation of (a) HT-1080 (b) HFF-1 assessed by AlamarBlue® assay. Cells were cultured on HA-Tyr/Gtn-HPA mixed hydrogel ($\Delta$) and HA-EGCG hydrogel ($\bigcirc$).

Representative photomicrographs of the cell morphology for HT-1080, Hep G2 and HFF-1 cultured on HA-EGCG hydrogels following incubation times of 24 hours (a), 48 hours (b), 96 hours (c) and 144 hours (d) are shown in FIGS. 5, 6 and 7, respectively. The HT-1080 and Hep G2 cell numbers were found to decrease in relation to incubation time on HA-EGCG hydrogel. HT-1080 and Hep G2 cells became more spherical at the same time, indicating that they became less viable after culturing on HA-EGCG hydrogel. On the other hand, it was observed that HFF-1 cells continued to proliferate until confluence (FIG. 7d). These observations are inherent in the quantification of cell spreading (in FIG. 4a,b, c) and AlamarBlue® assay (in FIG. 8a-b). FIG. 8a-b shows the metabolic activity of HT-1080 and HFF-1 cells on HA-EGCG and the control HA-Tyr/Gtn-HPA hydrogel. As shown in FIG. 8a, HT-1080 metabolic activity was found to decrease in relation to incubation time on HA-EGCG hydrogel. In contrast, no significant decrease of metabolic activity was found for HFF-1 cells plated on HA-EGCG (FIG. 8b).

Figure 9:
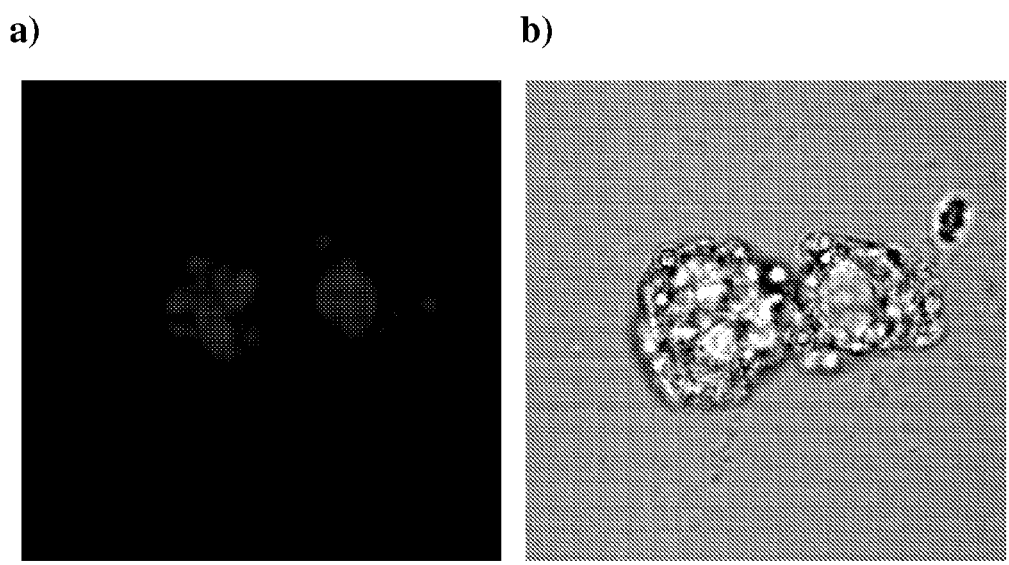
FIG. 9. DNA fragmentation assay for apoptosis. Nucleus morphology of cells cultured on HA-EGCG hydrogel after 120 h. The nuclei of Hep G2 cells were visualized by DAPI staining in blue (light grey regions in black and white image) (left image (a)). DNA fragmentation was observed using a fluorescence microscope with 200× power. Photo on the right is overlaid image of fluorescent probe and phase contrast (b).

The mechanism underlying the suppression in cancer proliferation by HA-EGCG is not well understood. In order to identify whether proliferation suppression is due to cellular senescence or by HA-EGCG induced apoptosis, a DNA fragmentation assay was performed, in which apoptosis was visualized by DAPI staining. As shown in FIGS. 9a and 9b, DNA fragmentation was observed in Hep G2 cells cultured on HA-EGCG hydrogel. This result indicated that HA-EGCG suppressed cancer proliferation through eliciting apoptosis, which in turn halts cell division cycle. In addition, no DNA fragmentation was observed in HFF-1 cells (data not shown).

HA-EGCG hydrogels did not induce any remarkable cytotoxicity against normal cells, but inhibited cell proliferation of carcinomas. EGCG has been shown to inhibit proteasomes in cancer cells. EGCG can therefore selectively inhibit cell proliferation and induce apoptosis in cancer cells without adversely affecting normal cells [26]. The chemopreventive activity and chemotherapeutic effects of HA-EGCG is expected, because tea polyphenols such as EGCG and theasinensin (EGCG oxide) are known to be capable of inducing apoptosis, as well inhibiting tumour cell growth and tumorigenesis [9, 27, 28]. Fujimura et al., [29] identified that the metastasis-associated 67 kDa laminin receptor (67LR) confers EGCG responsiveness to cancer cells and mediates the anticancer activity of EGCG. The selectivity in the anti-proliferation effect of HA-EGCG on cancer cells could possibly be 67LR mediated. Data from this study suggested that the potencies of EGCG may have been retained in the HA-EGCG hydrogel. Noda et al., [13] have shown that combined-treatment of a chemotherapeutic agent with EGCG synergistically induced apoptosis.

Figure 10:
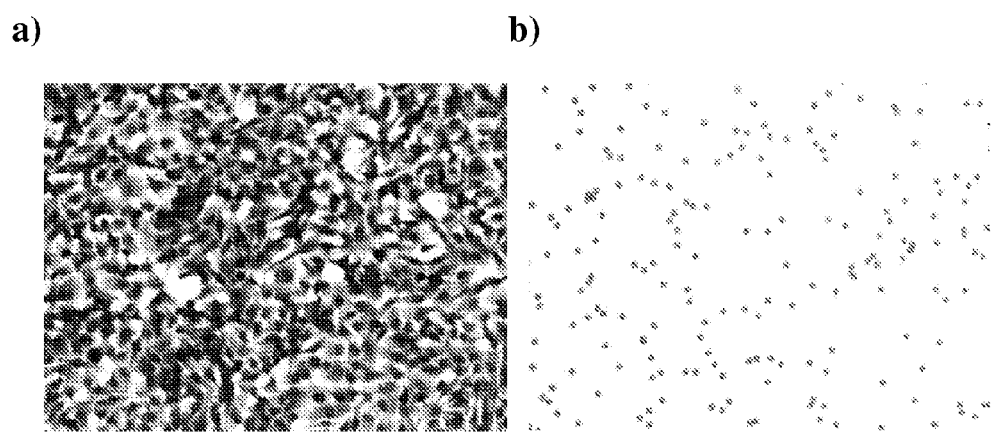
FIG. 10. Cell invasion assay. DiffQuik staining of migrated HT-1080 cells in Matrigel™ invasion chamber (left image (a)) and HA-ECGC hydrogel invasion chamber (right image (b)).

Invasion assay: With the aim of establishing anti-metastatic constructs capable of preventing cancer cells migration, an invasion assay was conducted to examine whether HA-EGCG hydrogels exert the anti-metastatic effect on tumor invasion which is known of EGCG. A Matrigel™ invasion assay was used as control. Pictures of typical fields of stained invading cells are shown in FIG. 10. Cells that migrated through Matrigel™ were stained (FIG. 10a). In contrast, no invading cells were found on the membrane underneath HA-EGCG hydrogel (FIG. 10b), implying possible anti-metastatic effects of the HA-EGCG hydrogel on HT-1080 migration. 67LR has been implicated in laminin-induced tumor cell attachment and migration, as well as tumor angiogenesis, invasion and metastasis [29]. The anti-metastatic effect of HA-EGCG could be 67LR mediated or it might be attributed to interactions of EGCG with MMP gelatinases leading to down-regulation of proliferation [11].

Figure 11:
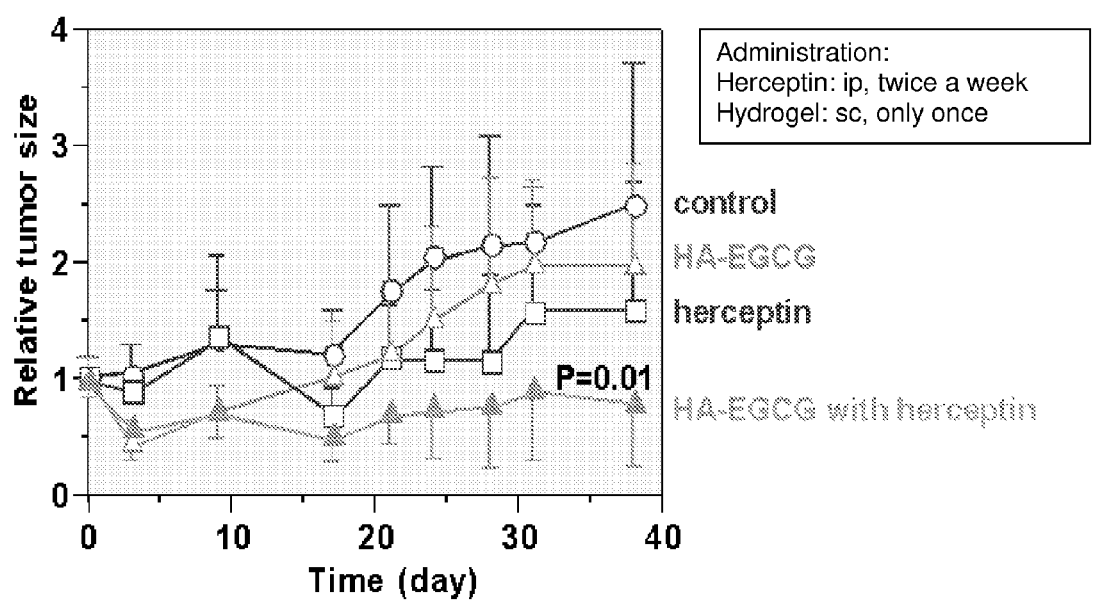
FIG. 11. Tumour growth inhibition of human breast BT474 cancer in mice. Mice were treated with control ($\bigcirc$), HA-EGCG hydrogel ($\Delta$), herceptin ($\square$) or herceptin loaded HA-EGCG hydrogel ($\blacktriangle$).

Animal study: Sustained release of herceptin from the HA-EGCG hydrogel demonstrated inhibition of tumour growth in mice with human breast cancer BT474 cells (FIG. 11).

Figure 12:
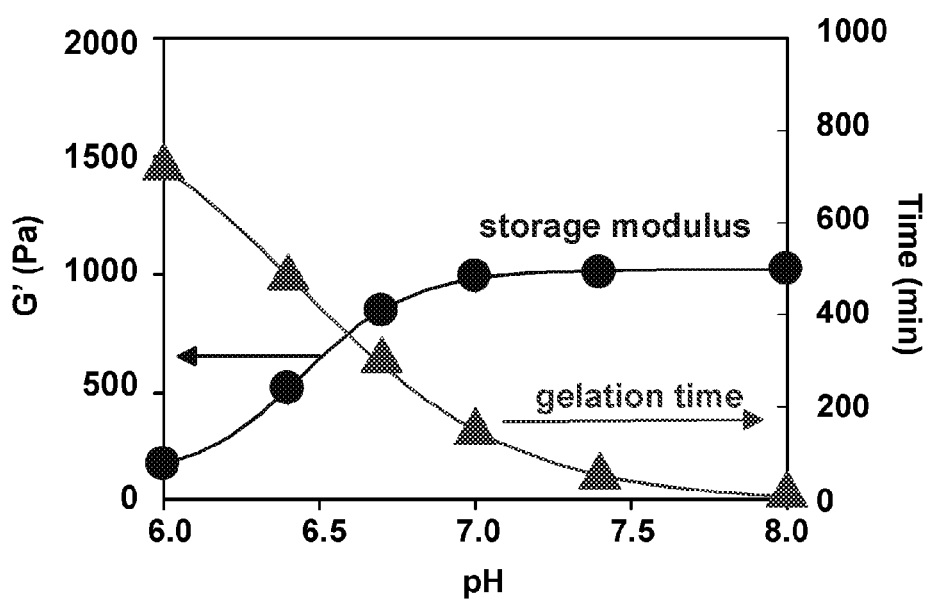
FIG. 12. Formation of HA-EGCG hydrogel through air-autoxidation at different pH. The gelation time of HA-EGCG hydrogels formed by air-autoxidation was reduced with increased pH.
Figure 13:
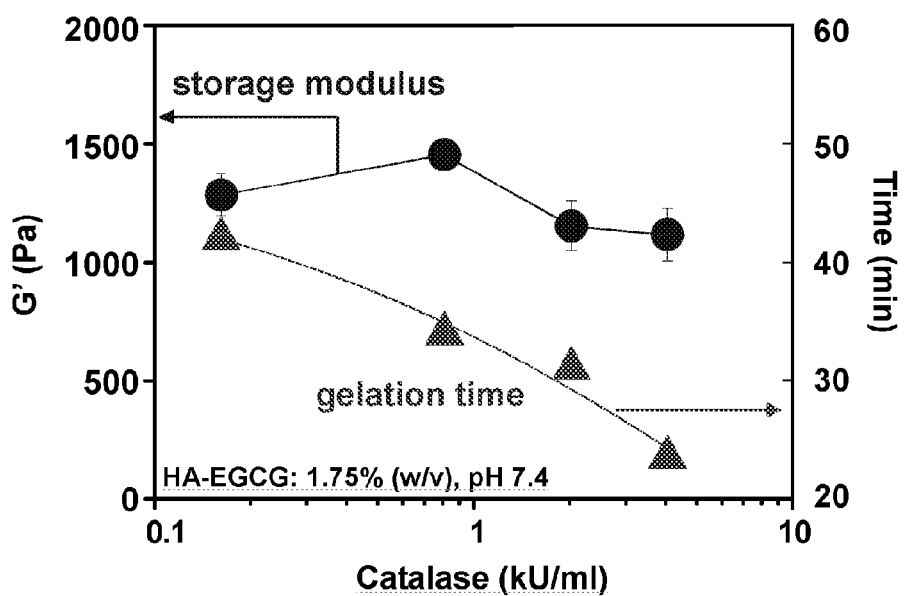
FIG. 13. Acceleration of HA-EGCG hydrogels through air-autoxidation by the addition of catalase. The gelation time decreased with increased catalase concentration.

Gelation time of auto-oxidation flavonoid conjugate hydrogel: The gelation time of HA-EGCG hydrogels formed by air-autoxidation reduced from 12 h at pH 6 to 10 min at pH 8 (FIG. 12). The storage modulus increased from 200 to 1000 Pa as the pH increased from 6 to 8. To speed up the air-oxidation process, the $H_2O_2$ generated by EGCG air-autoxidation was removed by the catalase, an enzyme that catalyzes the decomposition of hydrogen peroxide to water and oxygen. At pH 7.4, the gelation time decreased from 42 to 23 min as catalase concentration increased from 0.162 to 4 kU/ml (FIG. 13). The storage modulus was between 1000 to 1500 Pa.

Figure 14:
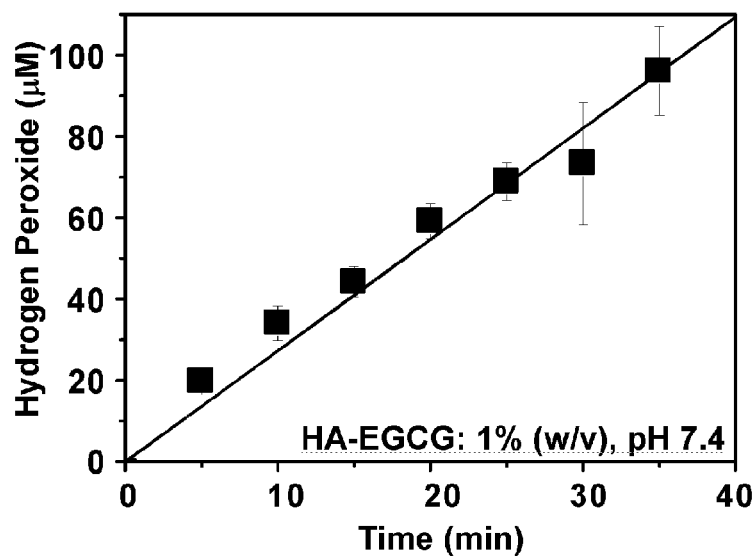
FIG. 14. Production of $H_2O_2$ by HA-EGCG conjugates. $H_2O_2$ generated by HA-EGCG during air-autoxidation increased with time and was observed in the micromolar range.
Figure 15:
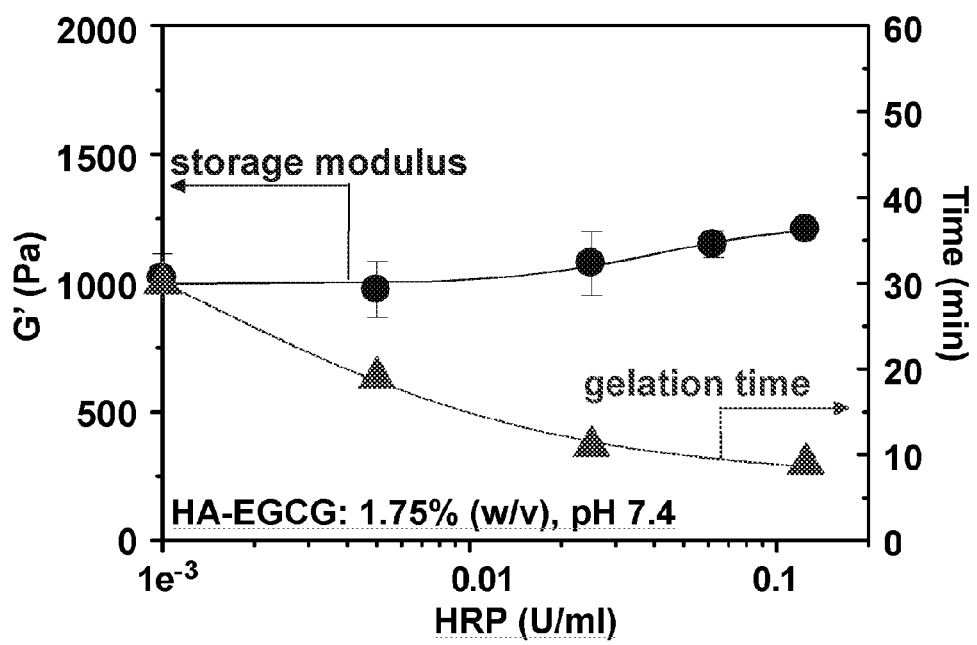
FIG. 15. Formation of HA-EGCG hydrogels by HRP-mediated crosslinking reaction without the addition of exogenous $H_2O_2$. At pH 7.4, the gelation time of HA-EGCG decreased with increased concentrations of HRP concentration.

Formation HRP-mediated crosslinking in the absence of exogenous $H_2O_2$: The amount of $H_2O_2$ generated by HA-EGCG during air-autoxidation increased with time and was found to be in the micromolar range (FIG. 14). At pH 7.4, the gelation time of HA-EGCG decreased from 50 to 9 min as the HRP concentration increased from 0 to 0.125 unit/ml (FIG. 15). The storage modulus was between 1000 to 1200 Pa.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

All technical and scientific terms used herein have the same meaning as commonly understood by one of ordinary skill in the art of this invention, unless defined otherwise.

Concentrations given in this specification, when given in terms of percentages, include weight/weight (w/w), weight/volume (w/v) and volume/volume (v/v) percentages.

As used in this specification, the singular forms "a", "an" and "the" include plural reference unless the context clearly dictates otherwise. As used in this specification, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit of the invention.

REFERENCES

[1] Reich, G., Pharmaceutical formulation and clinical application, Dubel, S., editor, in Handbook of Therapeutic Antibodies, vol 1: Wiley-VCH, Weinheim, 239-265 (2007).

[2] Liu, L., Sakaguchi, T., Kanda, T., Hitomi, J., Tabata, Y., Hatakeyama, K., Delivery of interleukin-12 in gelatin hydrogels effectively suppresses development of transplanted colonal carcinoma in mice, Cancer Chemotherapy & Pharmacology, 51, 53-57 (2003).

[3] Shimizu, T., Kishida, T., Hasegawa, U., Udea, Y., Imanishi, J., Yamagishi, H., Akiyoshi, K., Otsuji, E., Mazda, 0., Nanogel DDS enables sustained release of IL-12 for tumor immunotherapy, Biochemical & Biophysical Research Communication, 367, 330-335 (2008).

[4] Lee, F., Chung, J. E., Kurisawa, M., An injectable enzymatically crosslinked hyaluronic acid-tyramine hydrogel system with independent tuning of mechanical strength and gelation rate, Soft Matter (in press)

[5] Jankun, J., Selman, S. H., Swiercz, R., Why drinking green tea could prevent cancer, Nature, 387, 561 (1997).

[6] Garbisa, S., Biggin, S., Cavallarin, N., Sartor, L., Benelli, R., Albini, A., Tumor invasion: molecular shears blunted by green tea, Nature medicine, 5(11), 1216 (1999).

[7] Tachibana, H., Koga, K., Fujimura, Y., Yamada, K., A receptor for green tea polyphenol EGCG, Nature Structural & Molecular Biology, 11(4), 380-381 (2004).

[8] Nagle, D. G., Ferreira, D., Zhou, Y. D., Epigallocatechin-3-gallate (EGCG): chemical and biomedical perspectives, Phytochemistry, 67, 1849-1855 (2006).

[9] Sang, S., Yang, I., Buckley, B., Ho, C. T., Yang, C. S., Autooxidative quinine formation in vitro and metabolite formation in vivo from tea polyphenol (−)-epigallocatechin-3-gallate: studied by real-time mass spectrometry combined with tandem mass ion mapping, Free Radical Biology & Medicine, 43, 362-371 (2007).

[10] Yang, C. S., Wang, Z. Y., Tea and cancer, Journal of the National Cancer Institute, 85(13), 1038-1049 (1993).

[11] Garbisa, S., Sartor, L., Biggin, S., Salvato, B., Benelli, R., Albini, A., Tumor gelatinases and invasion inhibited by the green tea flavanol epigallocatechin-3-gallate, Cancer, 91(4), 822-832, (2001).

[1,2] Jobstl, E., O'Connell, J., Fairclough, P. A., Williamson, M. P., Molecular model for astringency produced by polyphenol protein interactions, Biomacromolecules, 5, 942-949 (2004).

[13] Noda, C., He, J., Takano, T., Tanaka, C., Kondo, T., Tohyama, K., Yamamura, H., Tohyama, Y., Induction of apoptosis by epigallocatechin-3-gallate in human lymphoblastoid B cells, Biochemical and Biophysical Research Communications, 362, 951-957 (2007).

[14] Tzircotis, G., Thorne, R. F., Isacke, C. M., Chemotaxis towards hyaluronan is dependent on CD44 expression and modulated by cell type variation in CD44-hyaluronan binding, Journal of Cell Science, 118, 5119-5128 (2005).

[15] Kurisawa, M., Chung, J. E., Yang, Y. Y., Gao, S. J., Uyama, H., Injectable biodegradable hydrogels composed of hyaluronic acid-tyramine conjugates for drug delivery and tissue engineering, Chemical Communications, 4312-4314 (2005).

[16] Kurisawa, M., Wang, L. S., Chung, J. E., Gelatin-phenol hydrogels for tissue engineering, US patent (in preparation).

[17] Jia, X., Colombo, G., Padera, R., Langer, R., Kohane, D. S., Prolongation of sciatic nerve blockade by in situ crosslinked hyaluronic acid, Biomaterials, 25, 4797-4804 (2004).

[18] Yeo, Y., Highley, C. B., Bellas, E., Ito, T., Marini, R., Langer, R., Kohane, D. S., In situ cross-linkable hyaluronic acid hydrogels prevent post-operative abdominal adhesions in a rabbit model, Biomaterials, 27, 4698-4705 (2006).

[19] Park, Y. D., Tirelli, N., Hubbell, J. A., Photopolymerized hyaluronic acid-based hydrogels and interpenetrating networks, Biomaterials, 24, 893-900 (2003).

[20] Chua, P. H., Neoh, K. G., Kang, E. T., Wang, W., Surface functionalization of titanium with hyaluronic acid/chitosan polyelectrolyte multilayers and RGD for promoting osteoblast functions and inhibiting bacterial adhesion, Biomaterials, 29, 1412-1421 (2008).

[21] Hou, Z., Sang, S., You, H., Lee, M. J., Kong, J., Chin, K. V., Yang, C. S., Mechanism of action of (−)-epigallocatechin-3-gallate: auto-oxidation-dependent inactivation of epidermal growth factor receptor and direct effects on growth inhibition in human esophageal cancer KYSE 150 cells, Cancer Research, 65(17), 8049-8056 (2005)

[22] Kobayashi, S., Uyama, H., Kimura, S., Enzymatic polymerization, Chemical Review, 101, 3793-3818 (2001)

[23] Bronzino, J. D., Tissue engineering and artificial organs, $3^{rd}$ ed., CRC Press, USA (2006)

[24] Engler, A. J., Richert, L., Wong, J. Y., Picart, C., Discher, D. E., Surface probe measurements of the elasticity of sectioned tissue, thin gels and polyelectrolyte multilayer films: Correlations between substrate stiffness and cell adhesion, Surface Science, 570, 142-154 (2004).

[25] Yeung, T., Georges, P. C., Flanagan, L. A., Marg, B., Ortiz, M., Funaki, M., Zahir, N., Ming, W., Weaver, V., Janmey, P. A., Effects of substrate stiffness on cell morphology, cytoskeletal structure, and Adhesion, Cell Motility and the Cytoskeleton, 60, 24-24 (2005).

[26] Smith, D. M., Wang, Z., Kazi, A., Li, L. H., Chan, T. H., Dou, Q. P., Synthetic analogs of green tea polyphenols as proteasome inhibitors, Molecular Medicine, 8(7), 382-392 (2002).

[27] Yang, C. S., Chung, J. Y., Yang, G. Y., Chhabra, S. K., Lee, M. J., Tea and tea polyphenols in cancer prevention, Journal of Nutrition, 130, 472S-478S (2000).

[28] Pan, M. H., Liang, Y. C., Lin-Shiau, S. Y., Zhu, N. Q., Ho, C. T., Lin, J. K., Induction of apoptosis by the oolong tea polyphenol theasinensin A through Cytochrome c release and activation of caspase-9 and caspase-3 in human U937 cells, Journal of Agriculture and Food Chemistry, 48, 6337-6346 (2000).

[29] Fujimura, Y., Yamada, K., Tachibana, H., A lipid raft-associated 67 kDa laminin receptor mediates suppressive effect of epigallocatechin-3-O-gallate on FcεRI expression, Biochemical & Biophysical Research Communications, 336, 674-681, (2005).

[30] Jankun J., et al. *Nature* 387, 561 (1997).

[31] Bodoni A. et al. *J. Nutr. Biochem.* 13, 103-111 (2002).

[32] Nakagawa K. et al. *J. Agric. Food Chem.* 47, 3967-3973 (1999).

[33] Terao J., et al. *Arch. Biochem. Biophys.* 308, 278-284 (1994).

[34] Isemura M., et al. *Biofactors* 13, 81-85 (2000).

[35] Ikeda I., et al. *J. Nutr.* 135, 155 (2005).

[36] Lill G., et al. *FEBS Letters* 546, 265-270 (2003).

[37] Sakanaka S, and Okada Y. *J. Agric. Food Chem.* 52, 1688-1692 (2004).

[38] Yokozawa T., et al., *J. Agric. Food Chem.* 48, 5068-5073 (2000).

[39] Yen G. C., et al. *J. Agric. Food Chem.* 45, 30-34 (1997).

[40] Yamanaka N., et al. *FEBS Lett.* 401, 230-234 (1997).

[41] Roedig-Penman A. and Gordon M. H. *J. Agric. Food Chem.* 1997, 45, 4267-4270.

[42] Zhao J., et al. *Carcinogenesis,* 1999, 20, 1737-1745.

[43] Ariga T. and Hamano M. *Agric. Biol. Chem.* 54, 2499-2504 (1990).

[44] Chung J. E., et al. *Biomacromolecules* 5, 113-118 (2004).

[45] Kurisawa M., et al. *Biomacromolecules* 4, 1394-1399 (2003).

[46] Hagerman A. E., et al. *J. Agric. Food Chem.* 46, 1887 (1998).

[47] Hagerman A. E., et al. *J. Agric. Food Chem.* 46, 1887 (1998).

[48] Li C. and Xie B. *J. Agric. Food Chem.* 48, 6362 (2000).

[49] Zhao J., et al. *Carcinogenesis,* 1999, 20, 1737-1745).

[50] Qui, Y. and Park, K. *Advanced Drug Delivery Reviews* 53, 321 (2001).

[51] Drury J. and Mooney, D. *Biomaterials* 24, 4337 (2003).

[52] Roginsky, V.; Alegria, A. E. Oxidation of tea extracts and tea catechins by molecular oxygen. *J Agric Food Chem* 53:4529-4535; 2005.

[53] Mochizuki, M.; Yamazaki, S.; Kano, K.; Ikeda, T. Kinetic analysis and mechanistic aspects of autoxidation of catechins. *Biochim Biophys Acta* 1569:35-44; 2002.

[54] Hou, Z.; Sang, S.; You, H.; Lee, M. J.; Hong, J.; Chin, K. V.; Yang, C. S. Mechanism of action of (−)-epigallocatechin-3-gallate: auto-oxidation-dependent inactivation of epidermal growth factor receptor and direct effects on growth inhibition in human esophageal cancer KYSE 150 cells. *Cancer Res* 65:8049-8056; 2005.

[55] Sang, S.; Lee, M. J.; Hou, Z.; Ho, C. T.; Yang, C. S. Stability of tea polyphenol (−)-epigallocatechin-3-gallate and formation of dimers and epimers under common experimental conditions. *J Agric Food Chem* 53:9478-9484; 2005.

[56] Kurisawa, M.; Chung, J. E.; Yang, Y. Y.; Gao, S. J.; Uyama, H. Injectable biodegradable hydrogels composed of hyaluronic acid-tyramine conjugates for drug delivery and tissue engineering. *Chem Commun (Camb)*: 4312-4314; 2005.

What is claimed is:

1. A method for producing a hydrogel that is capable of adhesion of cells and which comprises enzymatically cross-linked conjugates of a hydrogel forming agent and a flavonoid, the method comprising combining:
    (i) from about 0.1 mg/ml to about 500 mg/ml of conjugates of the hydrogel forming agent and the flavonoid;
    (ii) from about 0.001 mM to about 50 mM peroxide; and
    (iii) from about 0.001 units/ml to about 10 units/ml peroxidase;
thereby producing the hydrogel.

2. The method of claim 1, wherein the flavonoid is a catechin-based flavonoid.

3. The method of claim 1, wherein the flavonoid is epigallocatechin gallate.

4. The method of claim 1, wherein the hydrogel forming agent is a polymer.

5. The method of claim 1, wherein the hydrogel forming agent is hyaluronic acid.

6. The method of claim 1, further comprising combining a bioactive agent with said conjugates, peroxide and peroxidase.

7. The method of claim 6, wherein the bioactive agent is an anti-cancer agent.

* * * * *